(12) United States Patent
Hirst et al.

(10) Patent No.: US 10,774,262 B2
(45) Date of Patent: Sep. 15, 2020

(54) THREE-DIMENSIONAL STRUCTURES OF MESOGENIC LIGAND-FUNCTIONALIZED NANOPARTICLES AND METHODS OF MAKING AND USING THE SAME

(71) Applicant: The Regents of the University of California, Oakland, CA (US)

(72) Inventors: Linda Hirst, Merced, CA (US); Jason Hein, Vancouver (CA); Sayantani Ghosh, Merced, CA (US); Andrea Rodarte, Merced, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/535,259

(22) PCT Filed: Dec. 22, 2015

(86) PCT No.: PCT/US2015/067496
§ 371 (c)(1),
(2) Date: Jun. 12, 2017

(87) PCT Pub. No.: WO2016/106377
PCT Pub. Date: Jun. 30, 2016

(65) Prior Publication Data
US 2017/0362504 A1    Dec. 21, 2017

Related U.S. Application Data

(60) Provisional application No. 62/096,504, filed on Dec. 23, 2014.

(51) Int. Cl.
C09K 19/20    (2006.01)
C07C 217/22    (2006.01)
(Continued)

(52) U.S. Cl.
CPC ...... *C09K 19/2007* (2013.01); *B29C 35/0805* (2013.01); *C07C 217/22* (2013.01);
(Continued)

(58) Field of Classification Search
CPC ............ C09K 19/2007; C09K 11/88; C09K 2019/0444; C09K 2019/2035;
(Continued)

(56) References Cited

U.S. PATENT DOCUMENTS 5,097,463 A    5/1992    Wagenblast et al.
6,479,146 B1    11/2002    Caruso et al.
(Continued)

FOREIGN PATENT DOCUMENTS

JP    2013087308    5/2013
JP    2016029149    3/2016
(Continued)

OTHER PUBLICATIONS

Lewandowski et al "Control of Gold Nanoparticles superlattice properties via Mesogenic Ligand Architecture", Feb. 2019, 2013, Langmuir, 2013, V29, p. 3401-3410. (Year: 2013).*
(Continued)

*Primary Examiner* — Ruiyun Zhang
(74) *Attorney, Agent, or Firm* — Rudy J. Ng; Bozicevic, Field & Francis LLP

(57) ABSTRACT

Three-dimensional structures of stably associated mesogenic ligand-functionalized nanoparticles are provided. Compositions that include these structures, as well as methods of making the structures are also provided. The structures, compositions and methods find use in a variety of applications, such as light emitting devices (e.g., video displays, lights, etc.), inks, photonics and encapsulation technologies.

32 Claims, 6 Drawing Sheets

(51) Int. Cl.

| | | |
|---|---|---|
| *C07C 247/18* | (2006.01) | |
| *C09D 11/00* | (2014.01) | |
| *C09K 11/02* | (2006.01) | |
| *B29C 35/08* | (2006.01) | |
| *C09K 11/88* | (2006.01) | |
| *C09K 19/52* | (2006.01) | |
| *C09K 19/04* | (2006.01) | |
| *C08K 9/04* | (2006.01) | |
| *H01L 51/50* | (2006.01) | |
| *B29K 105/00* | (2006.01) | |

(52) U.S. Cl.
CPC ............ *C07C 247/18* (2013.01); *C09D 11/00* (2013.01); *C09K 11/025* (2013.01); *C09K 11/88* (2013.01); *B29K 2105/0079* (2013.01); *C08K 9/04* (2013.01); *C09K 2019/0444* (2013.01); *C09K 2019/2035* (2013.01); *C09K 2019/2078* (2013.01); *C09K 2019/521* (2013.01); *C09K 2019/523* (2013.01); *C09K 2219/00* (2013.01); *H01L 51/5012* (2013.01); *Y10T 428/10* (2015.01)

(58) Field of Classification Search
CPC ...... C09K 2019/2078; C09K 2019/521; C09K 2019/523; C09K 2219/00; B29C 35/0805; C07C 217/22; C07C 217/24718; B29K 2105/0079; Y10S 977/773
USPC ..... 428/1.1; 546/14; 977/773, 774, 778, 830
See application file for complete search history.

(56) References Cited

U.S. PATENT DOCUMENTS

| | | |
|---|---|---|
| 8,088,499 B1 | 1/2012 | Wang et al. |
| 8,802,150 B2 | 8/2014 | Pandit et al. |
| 9,196,682 B2 | 11/2015 | Jang et al. |
| 2010/0130659 A1 | 5/2010 | Lee et al. |
| 2010/0162494 A1 | 7/2010 | Muller et al. |
| 2011/0062385 A1 | 3/2011 | Hegmann et al. |
| 2013/0087738 A1 | 4/2013 | Jung |
| 2013/0105839 A1 | 5/2013 | Naasani et al. |
| 2013/0235290 A1 | 9/2013 | Takezoe et al. |
| 2014/0170214 A1 | 6/2014 | Scherman et al. |
| 2014/0371365 A1 | 12/2014 | Bae et al. |

FOREIGN PATENT DOCUMENTS

| | | |
|---|---|---|
| KR | 20140086058 | 7/2014 |
| WO | WO 2008070028 | 6/2008 |

OTHER PUBLICATIONS

De Filpo et al., (2012) "Alignment of single-walled carbon nanotubes in polymer dispersed liquid crystals," liquid crystal, Taylor & Francis 39(3): 359-364 XP001573222.

Broker et al., (2007) "Self-assembly of nanoparticles at interfaces," Soft Matter 3: 1231-1248.

Duan et al., (2005) "Magnetic Colloidosomes Derived from Nanoparticle Interfacial Self-Assenbly," Nano Letters 5(5): 949-952.

Liang et al., (2011) "Nematic-Smectic Transition under Confinement in Liquid Crystalline Colloidal Shells," Physical Review Letters 106(24): 247801-247804.

Rakovich and Donegan (2003) "Raman scattering and anti-Stokes emission from a single spherical microcavity with a CdTe quantum dot monolayer," Applied Physics Letters 83(13): 2539-2541.

Rodarte et al., (2014) "Tuning Quantum-Dot Organization in Liquid Crystals for Robust Photonic Applications," ChemPhysChem 15: 1413-1421.

Sander and Studart (2011) "Monodisperse Functional Colloidosomes with Tailored Nanoparticle Shells," Langmuir 27: 3301-3307.

Shi et al., (2005) "Gold Nanoshells on Polystyrene Cores for Control of Surface Plasmon Resonance," Langmuir 21(4): 1610-1617.

Chen, et al., Journal of Nanomaterials, Quantum Dots and Nanoparticles in Light Emitting Diodes, Displays, and Optoelectronic Devices, 2015, article ID 371679, 2 pages.

Murthy et al., International Journal of Nanomedicine, Nanoparticles in modern medicine: State of the art and future challenges, 2007:2(2) pp. 129-141.

Rodarte, et al., ChemPhysChem, Tuning Quantum-Dot Organization in Liquid Crystals for Robust Photonic Applications, 2014, 15, pp. 1413-1421.

Yazdi et al., Nano Biomed. Eng., Metal, Metalloid, and Oxide Nanoparticles for Therapeautic and Diagnostic Oncology, 2016:8(4), pp. 246-267.

\* cited by examiner

THREE-DIMENSIONAL STRUCTURES OF MESOGENIC LIGAND-FUNCTIONALIZED NANOPARTICLES AND METHODS OF MAKING AND USING THE SAME

CROSS-REFERENCE TO RELATED APPLICATIONS

This application claims priority pursuant to 35 U.S.C. § 119(e) to the filing date of U.S. Provisional Application No. 62/096,504, filed Dec. 23, 2014, the disclosure of which is incorporated herein by reference.

INTRODUCTION

Nanotechnology processes may be used to organize nanoparticles (NPs) of different types into well-ordered two- and three-dimensional assemblies on a macroscopic scale. In general, there are two different approaches to fabricating ordered arrays of NPs: top-down nanofabrication (i.e., lithographic techniques) or bottom-up self- or directed-assembly methods. For instance, top-down nanofabrication methods, such as nanolithography, begin with a substrate of a desired material, which is then protected by a mask and the exposed material is etched away. Depending upon the level of resolution required for features in the final product, etching of the base material can be done chemically using acids or mechanically using ultraviolet light, x-rays or electron beams. In contrast, bottom-up nanofabrication techniques place atoms or molecules one at a time to build the desired nanostructure. In some instances, it may be desirable to produce non-planar three-dimensional structures using materials and processes suitable for large-scale manufacturing.

Liquid crystals (LC) are anisotropic fluids in which the constituent molecules may have local directional order along an axis defined by a director, e.g., a dimensionless unit vector that represents the direction of preferred orientation of molecules in the neighborhood of any point. In some cases, liquid crystals may also have positional order, such as positional order along one direction. For example, liquid crystals in a smectic phase may have directional order along an axis as described above, while also being positionally ordered into layers. The liquid crystals may retain their liquid-like properties within the layers. The temperature range of liquid crystal phases exhibited by a material can be fine-tuned by controlling the molecular structure or by mixing the material with different LC or non-LC molecules, producing a variety of LC phases. Common liquid crystal phases include, for example: the nematic phase, which is well known for its use in display technologies and in which the liquid crystals have directional order but no positional order; the layered smectic phase described above; and the isotropic phase in which the liquid crystals have no directional or positional order.

SUMMARY

Three-dimensional structures of stably associated mesogenic ligand-functionalized nanoparticles are provided. Compositions that include these structures, as well as methods of making the structures are also provided. The structures, compositions and methods find use in a variety of applications, such as light emitting devices (e.g., video displays, lights, etc.), inks, photonics and encapsulation technologies.

Embodiments of the present disclosure include a three-dimensional structure of stably associated mesogenic ligand-functionalized nanoparticles.

In some embodiments, the structure has a shell configuration. In some embodiments, the shell configuration has the configuration of a spherical surface.

In some embodiments, the structure has a dimension (e.g., length) of 0.01 µm to 10 µm.

In some embodiments, the spherical surface has an average diameter of 0.01 µm to 10 µm.

In some embodiments, the nanoparticles have an average diameter of 1 nm to 100 nm.

In some embodiments, the nanoparticles are composed of a material selected from a semiconductor material, a metal, a metal oxide, a metalloid, an oxide, a magnetic material, and a polymer, or combinations thereof.

In some embodiments, the structure is composed of nanoparticles having substantially the same physical and chemical characteristics. In some embodiments, the structure is composed of nanoparticles having different physical and/or chemical characteristics.

In some embodiments, the mesogenic ligand-functionalized nanoparticles include a mesogenic ligand attached to a surface of the nanoparticles. In some embodiments, the mesogenic ligand includes a cross-linkable functional group. In some embodiments, the cross-linkable functional group is a light activated cross-linkable functional group.

In some embodiments, the mesogenic ligand has a structure of formula (I):

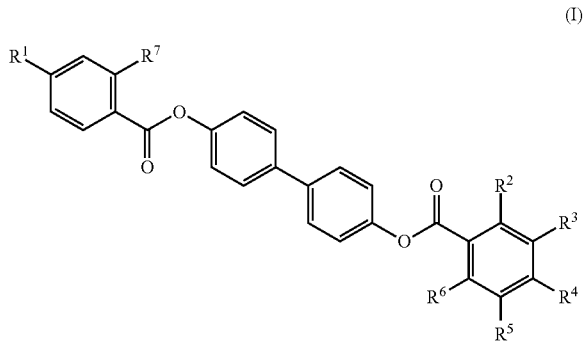

wherein $R^1$ to $R^7$ are each independently selected from H, halo, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, and substituted heteroaryl.

In some embodiments, the mesogenic ligand is one of the following ligands:

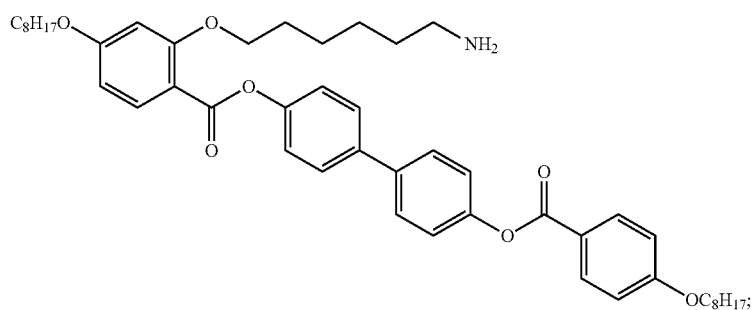
(L1)
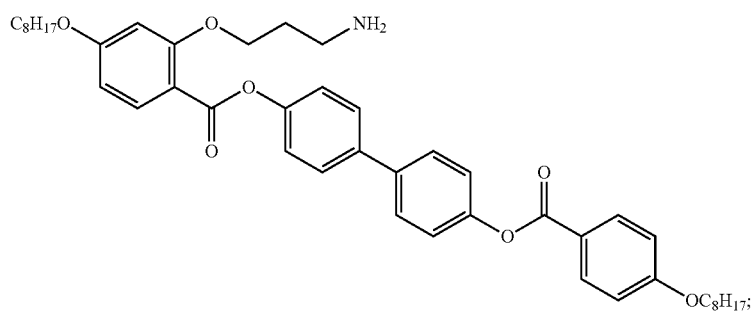
(L2)
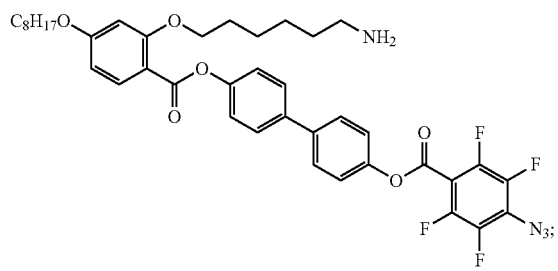
(L3)
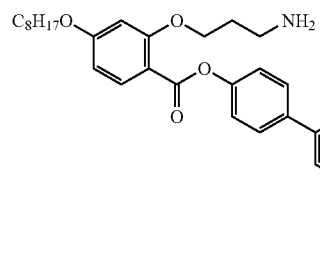
(L4)
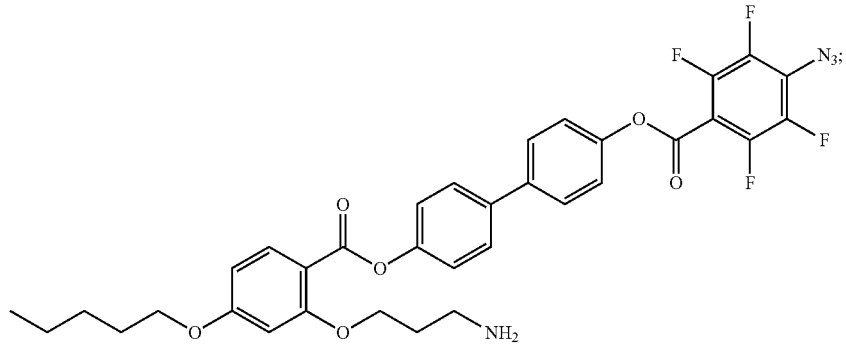
(L5)
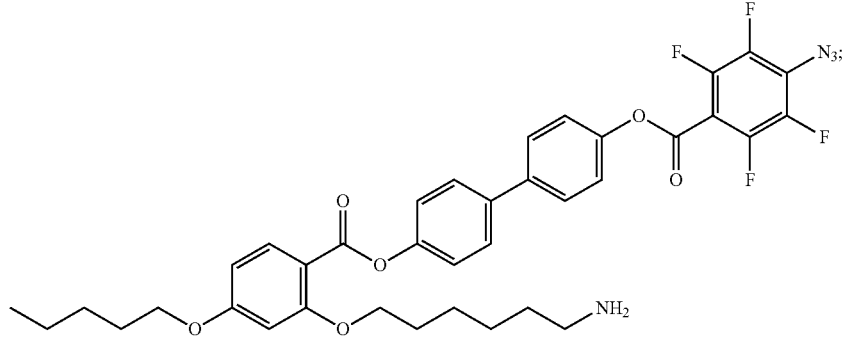
(L6)

-continued
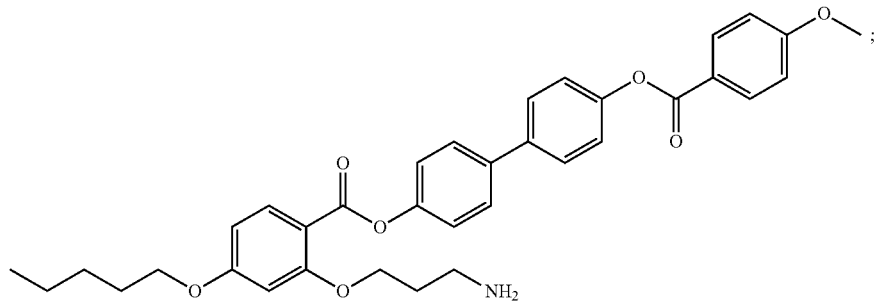
(L7)
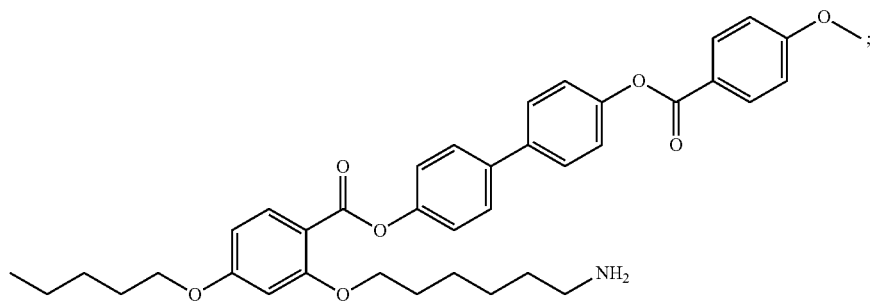
(L8)
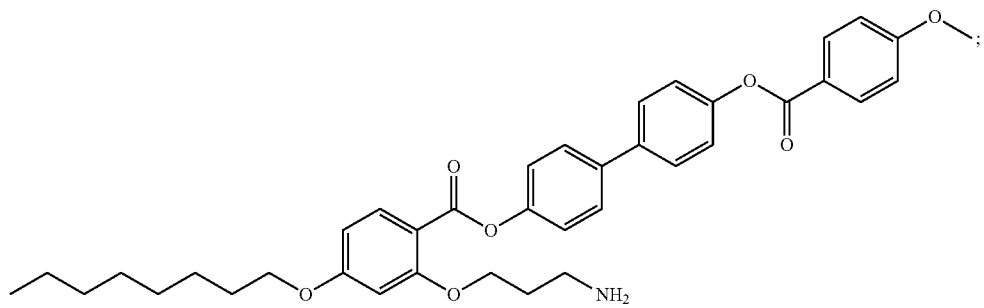
(L9)
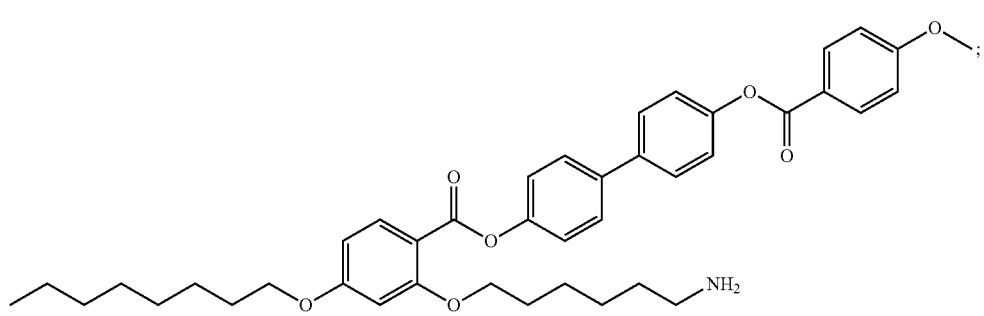
(L10)
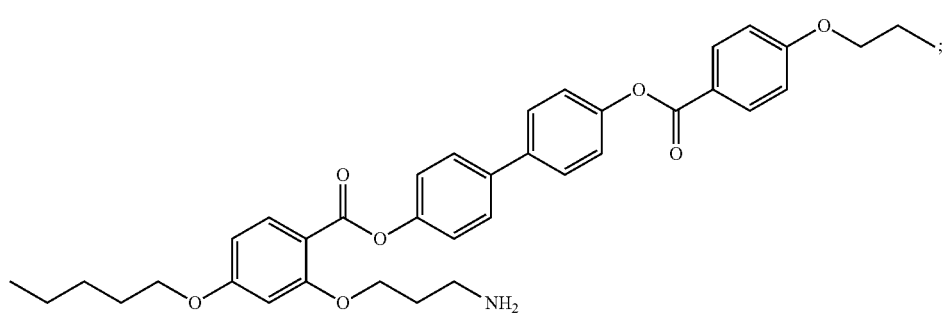
(L11)

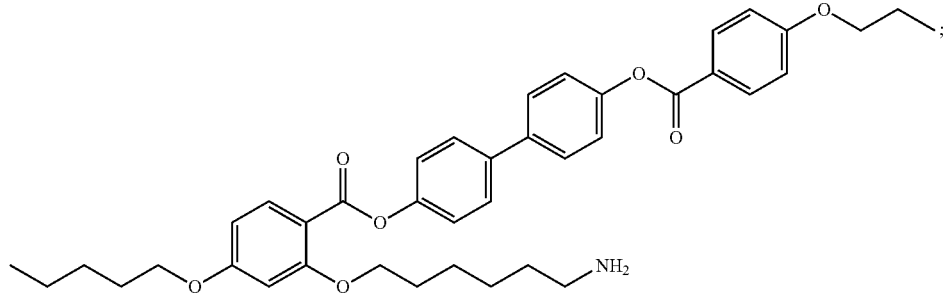
(L12)
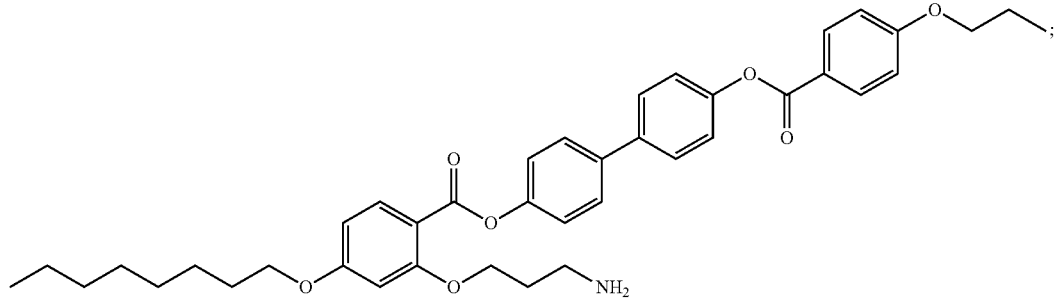
(L13)
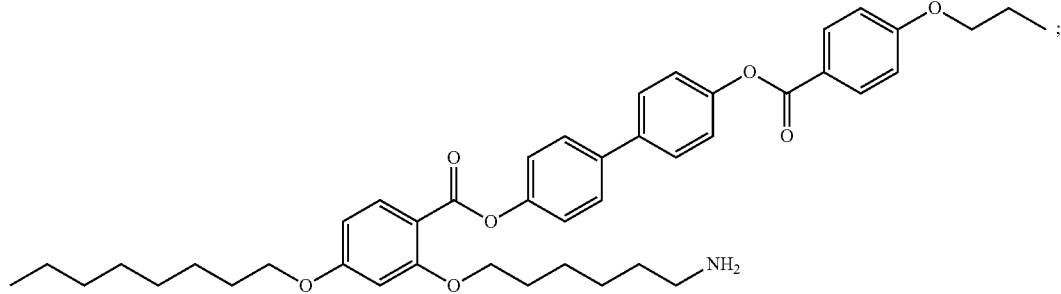
(L14)
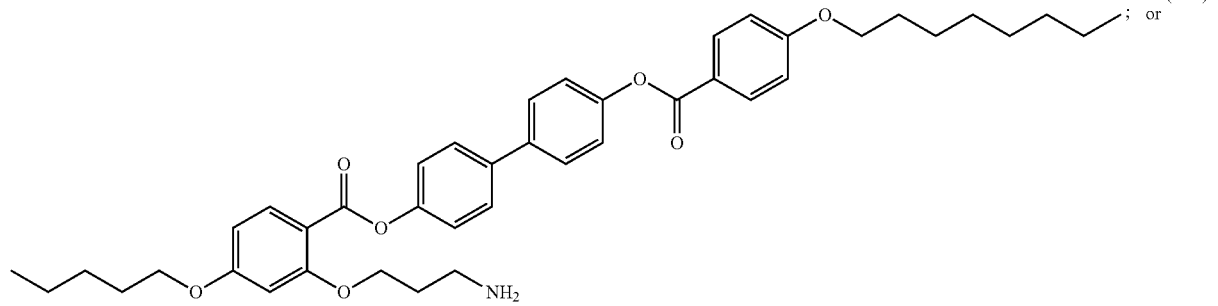
(L15) or
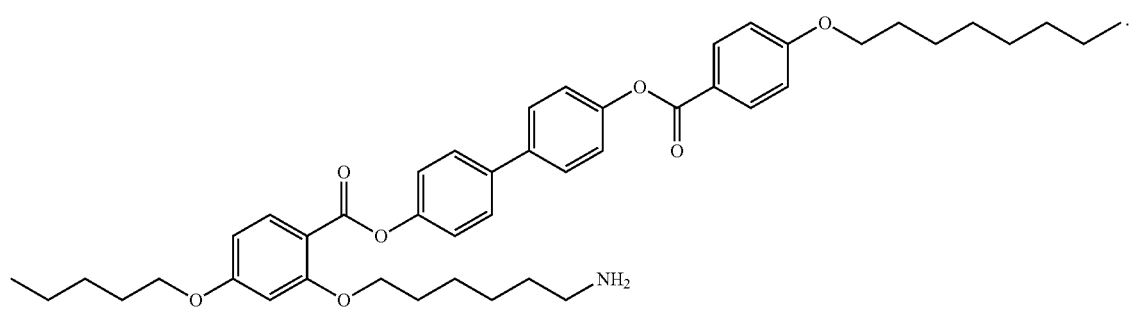
(L16)

In some embodiments, the three-dimensional structure of stably associated mesogenic ligand-functionalized nanoparticles includes an active agent encapsulated inside the structure.

In some embodiments, the three-dimensional structure of stably associated mesogenic ligand-functionalized nanoparticles includes an ink encapsulated inside the structure.

Aspects of the present disclosure include a composition that includes a liquid, and a three-dimensional structure of stably associated mesogenic ligand-functionalized nanoparticles in the liquid. In some embodiments, the liquid is an organic solvent. In some embodiments, the liquid is a liquid crystalline liquid.

Aspects of the present disclosure include a composition for producing a three-dimensional structure of stably associated mesogenic ligand-functionalized nanoparticles. The composition includes mesogenic ligand-functionalized nanoparticles, and a liquid crystalline liquid.

In some embodiments, a mesogenic ligand of the mesogenic ligand-functionalized nanoparticles has a phase transition temperature greater than the phase transition temperature of the liquid crystalline liquid.

Aspects of the present disclosure include a method of producing a three-dimensional structure of stably associated mesogenic ligand-functionalized nanoparticles. The method includes dispersing mesogenic ligand-functionalized nanoparticles in a liquid crystalline liquid, and inducing a phase transition in the liquid crystalline liquid to produce a three-dimensional structure of stably associated mesogenic ligand-functionalized nanoparticles.

In some embodiments, the dispersing includes applying sound energy to the mesogenic ligand-functionalized nanoparticles in the liquid crystalline liquid.

In some embodiments, the inducing includes reducing the temperature of the liquid crystalline liquid.

In some embodiments, the phase transition in the liquid crystalline liquid is a phase transition from an isotropic phase to a nematic phase.

In some embodiments, the mesogenic ligand-functionalized nanoparticles include a mesogenic ligand attached to a surface of the nanoparticles. In some embodiments, the mesogenic ligand includes a cross-linkable functional group. In some embodiments, the cross-linkable functional group is a light activated cross-linkable functional group. In some embodiments, the method includes applying light to the nanoparticles sufficient to activate the light activated cross-linkable functional group and produce one or more cross-links between the nanoparticles.

In some embodiments, the mesogenic ligand has a phase transition temperature greater than the phase transition temperature of the liquid crystalline liquid.

Aspects of the present disclosure include a composition that includes a three-dimensional structure of stably associated mesogenic ligand-functionalized nanoparticles produced by the methods disclosed herein.

Aspects of the present disclosure include a light emitting device that includes a substrate, and a three-dimensional structure of stably associated mesogenic ligand-functionalized nanoparticles as disclosed herein on a surface of the substrate.

In some embodiments, the light emitting device is a component of a video display or a light.

BRIEF DESCRIPTION OF THE DRAWINGS

FIG. 2, panel B, shows a fluorescence microscopy image showing QD distribution for a few shells. FIG. 2, panel C, shows a polarized optical microscopy image of the same sample area shown in FIG. 2, panel B. The polarizers were crossed as indicated by the white arrows and the material was oriented such that the nematic director, n, was parallel to one of the polarizers as shown highlighting topological defects around the shells. A rubbed PVA alignment layer was used to provide planar alignment for this sample. 'Saturn-ring' and 'bipolar' defects were observed. QD shells prepared using ligand L2 were stable at room temperature, as shown in FIG. 2, panel D. The QD shells began to disperse at 115° C., as shown in FIG. 2, panel E, and at 120° C., as shown in FIG. 2, panel F. As shown in FIG. 2, panel G, QD shells reformed at room temperature after re-cooling.

FIG. 3, panel A, shows dense nanoparticle (NP) packing within fragments of a large shell after toluene extraction (image width, 1.4 µm). FIG. 3, panel B, shows a wider field image (width, 3.8 µm) of shells of the same composition in 4-cyano-4'-pentylbiphenyl (5CB). FIG. 3, panel C, shows a FFT of a 0.67 µm wide area in the center of the large fragment. FIG. 3, panel D, shows a graph of X-ray scattering data for QD shells with ligand L1 in nematic liquid crystal radially integrated. FIG. 3, panel E, shows a CCD scattering pattern corresponding to the data in FIG. 3, panel D. FIG. 3, panel F, shows a graph of a comparison of peak A for two different ligands L1 and L2.

FIG. 4, panel F, shows schematic representations of the process. Ligand organization around the finished shells was confirmed by the presence of saturn-ring defects, as shown in FIG. 4, panel G, as observed experimentally using polarized optical microscopy (see FIG. 2, panel C). FIG. 4, panel H, shows the structure for the QD shell—QDs pack closely with a tactoidal ligand arrangement to form the shell wall and liquid crystal (LC) ligands orient to create planar surface anchoring.

FIG. 5, panel B, shows an example of intact shells in toluene. FIG. 5, panel C and FIG. 5, panel D, show examples of split shells made of QDs functionalized with ligand L4 after toluene evaporation.

TERMS

Figure 1:
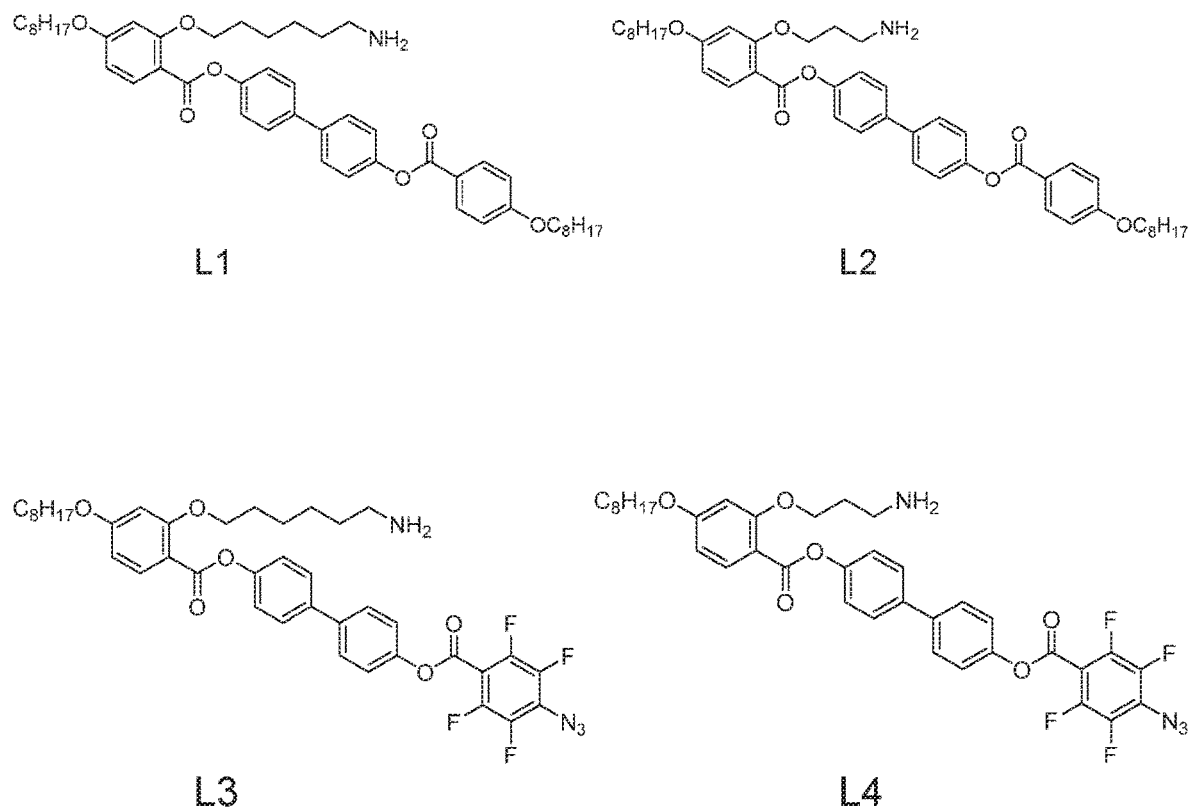
FIG. 1 shows the molecular structures of mesogenic ligands, L1, L2, L3 and L4, according to embodiments of the present disclosure.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), and neopentyl ((CH$_3$)$_3$CCH$_2$—).

The term "substituted alkyl" refers to an alkyl group as defined herein wherein one or more carbon atoms in the alkyl chain (except for the C$_1$ carbon) have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring.

This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like. The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$- moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

Unless indicated otherwise, the nomenclature of substituents that are not explicitly defined herein are arrived at by naming the terminal portion of the functionality followed by the adjacent functionality toward the point of attachment. For example, the substituent "aminoalkoxy" refers to the group NH$_2$-(alkyl)-O—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

DETAILED DESCRIPTION

Three-dimensional structures of stably associated mesogenic ligand-functionalized nanoparticles are provided. Compositions that include these structures, as well as methods of making the structures are also provided. The structures, compositions and methods find use in a variety of applications, such as light emitting devices (e.g., video displays, lights, etc.), inks, photonics and encapsulation technologies.

Three-Dimensional Structures

Aspects of the present disclosure include three-dimensional structures composed of nanoparticles. By "nanoparticles" is meant particles that have a size range in the nanometer (nm) scale. For example, a nanoparticle may have a size (e.g., largest dimension) of 1000 nm or less, such as a size ranging from 0.1 nm to 1000 nm. Three-dimensional structures of the present disclosure include structures having a shape that extends in three dimensions, such as length, width and height. Three-dimensional structures are distinct from one-dimensional structures (e.g., linear structures) and two-dimensional structures (e.g., planar structures).

In certain embodiments, three-dimensional structures of the present disclosure include structures having a shell configuration. The term "shell" or "shell configuration" as used herein describes structures where a surface at least partially, and sometimes completely, encloses a space or material. A shell or shell configuration may also be referred to as a "vesicle" or a "capsule". A shell may partially or completely enclose the space or material. For instance, a shell may partially enclose the space or material, such as enclose 50% or more of the space or material, or 60% or more, or 70% or more, or 80% or more, or 90% or more, or 95% or more, or 97% or more, or 99% or more of the space or material. Partial enclosure of a space or material includes embodiments where the surface is substantially contiguous and has one or more voids (e.g., holes) in the surface, and also includes embodiments where the surface is substantially continuous but the surface does not extend to completely enclose the space or material. In other embodiments, the shell completely encloses the space or material, such that the surface is substantially continuous without significant discontinuities (e.g., voids or holes) in the surface.

Surfaces with a shell configuration may have various shapes and sizes. For instance, shell configurations include, but are not limited to, regular shapes such as spherical shells, ellipsoid shells, cylinder shells, cone shells, cube shells, cuboid shells, pyramidal shells, torus shells, and the like. In other embodiments, the shell may have an irregular shape. In certain embodiments, structures of the present disclosure have a shell configuration, where the shell configuration is a spherical surface (i.e., a spherical shell). In certain embodiments, the structures of the present disclosure are microstructures. By "microstructure" or "microshell" or "microshell configuration" is meant the structure has a size range in the micrometer (μm) scale. For example, a microstructure may have a size (e.g., largest dimension) of 1000 μm or less, such as a size ranging from 10 nm to 1000 μm.

In certain embodiments, the structures are microstructures as described above, where the microstructures have a size of 1000 μm or less, such as 950 μm or less, or 900 μm or less, or 850 μm or less, or 800 μm or less, or 750 μm or less, or 700 μm or less, or 650 μm or less, or 600 μm or less, or 550 μm or less, or 500 μm or less, or 450 μm or less, or 400 μm or less, or 350 μm or less, or 300 μm or less, or 250 μm or less, or 200 μm or less, or 150 μm or less, or 100 μm or less, or 90 μm or less, or 80 μm or less, or 70 μm or less, or 60 μm or less, or 50 μm or less, or 40 μm or less, or 30 μm or less, or 20 μm or less, or 10 μm or less, or 9 μm or less, or 8 μm or less, or 7 μm or less, or 6 μm or less, or 5 μm or less, or 4 μm or less, or 3 μm or less, or 2 μm or less, or 1 μm or less, or 0.75 μm or less, or 0.5 μm or less, or 0.25 μm or less, or 0.1 μm or less, or 0.075 μm or less, or 0.05 μm or less, or 0.025 μm or less, or 0.01 μm or less. In some instances, the microstructures have a size ranging from 0.01 μm to 1000 μm, 0.025 μm to 1000 μm, 0.05 μm to 1000 μm, 0.075 μm to 1000 μm, 0.1 μm to 1000 μm, such as from 0.25 μm to 1000 μm, or 0.5 μm to 1000 μm, or 0.5 μm to 900 μm, or 0.5 μm to 800 μm, or 0.5 μm to 700, or 0.5 μm to 600 μm, or 0.5 μm to 500 μm, or 0.5 μm to 400 μm, or 0.5 μm to 300 μm, or 0.5 μm to 250 μm, or 0.5 μm to 200 μm, or 0.5 μm to 150 μm, or 0.5 μm to 100 μm, or 0.5 μm to 90 μm, or 0.5 μm to 80 μm, or 0.5 μm to 70 μm, or 0.5 μm to 60 μm, or 0.5 μm to 50 μm, or 0.5 μm to 40 μm, or 0.5 μm to 30 μm, or 0.5 μm to 20 μm, or 0.5 μm to 10 μm, or 0.5 μm to 9 μm, or 0.5 μm to 8 μm, or 0.5 μm to 7 μm, or 0.5 μm to 6 μm, or 0.5 μm to 5 μm, or 0.5 μm to 4 μm, or 0.5 μm to 3 μm, or 0.5 μm to 2 μm, or 0.5 μm to 1 μm. The size of the microstructures may be measured as the largest dimension of the microstructure (e.g., length, width, or height), or for spherical microstructures (e.g., spherical surfaces), may be measured as the average diameter of the microstructures. By "average" is meant the arithmetic mean. In certain instances, the microstructures have an average size of 5 μm. In certain instances, the microstructures have an average size of 1 μm. In certain instances, the microstructures have an average size of 0.1 μm. In certain instances, the microstructures have an average size of 0.05 μm. Mixtures of different sizes and/or shapes of three-dimensional structures (e.g., three-dimensional microstructures) may be used as desired. In other embodiments, the three-dimensional microstructures have substantially the same size and shape.

Three-dimensional structures of the present disclosure are composed of nanoparticles. For example, where the structure has a shell configuration, the shell may be composed of the nanoparticles. In certain embodiments, the nanoparticles are stably associated with each other to form the shell. By "stably associated" is meant that a moiety is bound to or otherwise associated with another moiety or structure under standard conditions. In certain instances, the nanoparticles may be stably associated with each other such that the shell substantially maintains its shape after formation of the shell. In some embodiments, the nanoparticles are stably associated with each other through non-covalent interactions, such as, but not limited to, ionic bonds, hydrophobic interactions, hydrogen bonds, van der Waals forces (e.g., London dispersion forces), dipole-dipole interactions, and the like. In some embodiments, the nanoparticles are stably associated with each other through covalent bonds. For example, a nanoparticle may be covalently bound or cross-linked to one or more nanoparticles in the shell. In certain cases, the nanoparticles are stably associated with each other through a combination of non-covalent and covalent interactions.

As described above, the three-dimensional structures of the present disclosure may be composed of nanoparticles. The nanoparticles may have a size of 1000 nm or less, such as 900 nm or less, or 800 nm or less, or 700 nm or less, or 600 nm or less, or 500 nm or less, or 400 nm or less, or 300 nm or less, or 250 nm or less, or 200 nm or less, or 150 nm or less, or 100 nm or less, or 90 nm or less, or 80 nm or less, or 70 nm or less, or 60 nm or less, or 50 nm or less, or 40 nm or less, or 30 nm or less, or 20 nm or less, or 10 nm or less, or 9 nm or less, or 8 nm or less, or 7 nm or less, or 6 nm or less, or 5 nm or less, or 4 nm or less, or 3 nm or less, or 2 nm or less, or 1 nm or less. In some instances, the nanoparticles have a size ranging from 0.1 nm to 1000 nm, such as from 0.5 nm to 1000 nm, or 1 nm to 1000 nm, or 1 nm to 900 nm, or 1 nm to 800 nm, or 1 nm to 700 nm, or 1 nm to 600 nm, or 1 nm to 500 nm, or 1 nm to 400 nm, or 1 nm to 300 nm, or 1 nm to 250 nm, or 1 nm to 200 nm, or 1 nm to 150 nm, or 1 nm to 100 nm, or 1 nm to 90 nm, or 1 nm to 80 nm, or 1 nm to 70 nm, or 1 nm to 60 nm, or 1 nm to 50 nm, or 1 nm to 40 nm, or 1 nm to 30 nm, or 1 nm to 20 nm, or 1 nm to 10 nm, or 1 nm to 9 nm, or 1 nm to 8 nm, or 1 nm to 7 nm, or 1 nm to 6 nm, or 1 nm to 5 nm. The size of the nanoparticles may be measured as the largest dimension of the nanoparticle (e.g., length, width, etc.), or for spherical nanoparticles, may be measured as the average diameter of the nanoparticles. By "average" is meant the arithmetic mean. In certain instances, the nanoparticles have an average size of 5 nm. In certain instances, the nanoparticles have an average size of 6 nm. Mixtures of different sizes and/or shapes of nanoparticles may be included in the three-dimensional structures as desired. In other embodiments, the nanoparticles have substantially the same size and shape.

Nanoparticles may have various shapes, such as, but not limited to, spherical, ellipsoid, cylinder, cone, cube, cuboid, pyramidal, needle, and the like. The nanoparticles may be made of any convenient material, such as, but not limited to, a semiconductor material, a metal, a metal oxide, a metalloid, an oxide, a magnetic material, a polymer, combinations thereof, and the like. For example, nanoparticles may be composed of materials, such as, but not limited to, titanium dioxide, silicon, gold, gold-plated silica, polymers, polymer-coated nanoparticles, quantum dot materials (as described in more detail below), and the like.

In certain embodiments, the nanoparticles that form the three-dimensional structure are arranged as a mixture of nanoparticles to form the three-dimensional structure. For instance, the three-dimensional structure may be composed of a mixture (e.g., a substantially homogeneous mixture) of nanoparticles. In some embodiments, the nanoparticles are arranged in one or more layers to form the three-dimensional structure. The composition of each layer of the three-dimensional structure may be the same or may be different. For example, each layer of the three-dimensional structure may be composed of the same type of nanoparticle or mixture of nanoparticles. Nanoparticles that are of the same type may include nanoparticles that are substantially the same with respect to their physical and chemical characteristics, such as, but not limited to, size, shape, composition, ligand attached to the surface of the nanoparticle, and the like. In other cases, a layer of the three-dimensional structure may have a different composition (e.g., a different nanoparticle or mixture of nanoparticles) than an adjacent layer. For instance, nanoparticles may differ with respect to one or more physical and/or chemical characteristics, such as, but not limited to, size, shape, composition, ligand attached to the surface of the nanoparticle, and the like.

In certain embodiments, the three-dimensional structure is composed of nanoparticles where the nanoparticles are a mixture of different types of nanoparticles. For instance, the mixture of nanoparticles may be a heterogeneous mixture of nanoparticles that is composed of different types of nanoparticles. The different types of nanoparticles may include nanoparticles that vary in one or more physical and/or chemical characteristics, such as, but not limited to, size, shape, composition, ligand attached to the surface of the nanoparticle, combinations thereof, and the like.

In certain embodiments, the nanoparticles are composed of a semiconductor material. For example, the nanoparticles may be quantum dots (QD). Quantum dots are nanoparticles made of a semiconductor material that exhibits quantum mechanical properties. In some instances, the nanoparticles may be composed of a material, such as, but not limited to, lead sulfide, lead selenide, cadmium selenide, cadmium sulfide, indium arsenide, indium phosphide, cadmium selenide sulfide, zinc sulfide, combinations thereof, and the like. In certain embodiments, the nanoparticles are composed of cadmium selenide (CdSe), zinc sulfide, or combinations thereof.

In certain embodiments, the nanoparticle is composed of a material or mixture of materials, such that the composition of the nanoparticle is substantially homogeneous. In some cases, the nanoparticle is composed of two or more materials. Nanoparticles composed of two or more materials include nanoparticles composed of a mixture of the two or more materials, such that the nanoparticles have a substantially homogeneous composition, and nanoparticles where the nanoparticles are composed of regions of a material interspersed with or adjacent to regions of one or more different materials. For instance, a nanoparticle may be composed of a core of a first material (or mixture of materials) substantially surrounded by a shell of a different material (or different mixture of materials). The shell of the different material may be disposed as one or more layers of material on a surface of the core of the first material.

In some embodiments, the nanoparticles may be quantum dots as described above. The quantum dots may be composed of two or more semiconductor materials, such as, but not limited to, lead sulfide, lead selenide, cadmium selenide, cadmium sulfide, indium arsenide, indium phosphide, cadmium selenide sulfide, zinc sulfide, and the like. In certain embodiments, the nanoparticle includes a core of cadmium selenide (CdSe) substantially surrounded by a shell of zinc sulfide (ZnS) disposed on a surface of the core.

In certain embodiments, the nanoparticles are functionalized nanoparticles. A functionalized nanoparticle is a nanoparticle that includes a ligand attached to the surface of the nanoparticle. The ligand may be attached to the surface of the nanoparticle through non-covalent interactions, such as, but not limited to, ionic bonds, hydrophobic interactions, hydrogen bonds, van der Waals forces (e.g., London dispersion forces), dipole-dipole interactions, and the like, or through covalent bonds. In certain embodiments, the ligand is attached to the surface of the nanoparticle through a covalent bond.

Ligands suitable for functionalization of the nanoparticles may vary depending on the desired properties of the functionalized nanoparticle. For example, the ligand on the ligand functionalized nanoparticle may be selected such that the spacing between adjacent ligand functionalized nanoparticles is a desired spacing. Stated another way, in some instances, the spacing between adjacent ligand functionalized nanoparticles may depend on one or more properties of the ligand, such as, but not limited to, the size, structure, and/or orientation of the ligand. In some cases, the spacing between adjacent nanoparticles is 5 nm or more, such as 6 nm or more, or 7 nm or more, or 8 nm or more, or 9 nm or more, or 10 nm or more, or 11 nm or more, or 12 nm or more, or 13 nm or more, or 14 nm or more, or 15 nm or more, or 16 nm or more, or 17 nm or more, or 18 nm or more, or 19 nm or more, or 20 nm or more. In some cases, the spacing between adjacent nanoparticles is 10 nm or more. In some cases, the spacing between adjacent nanoparticles is 5 nm to 20 nm, such as 7 nm to 15 nm, or 10 nm to 15 nm. In some instances, the spacing between adjacent nanoparticles is 10 nm to 15 nm, such as 10 nm to 13 nm, or 10 nm to 12 nm. In certain embodiments, the spacing between adjacent nanoparticles is selected so as to minimize shifts in the emission spectrum of the nanoparticles. In certain embodiments, the spacing between adjacent nanoparticles is selected so as to minimize energy losses due to fluorescence resonance energy transfer (FRET).

In certain embodiments, the ligand is a mesogenic ligand (also referred to as a liquid crystal ligand), and as such the functionalized nanoparticles are mesogenic ligand-functionalized nanoparticles. In some instances, a mesogenic ligand has liquid crystalline properties. For instance, a mesogenic ligand may include a rigid moiety and one or more flexible moieties. The rigid and flexible moieties of the mesogenic ligands may facilitate alignment of the mesogenic ligands in a common direction. For example, as described herein, mesogenic ligand-functionalized nanoparticles may be dispersed in a liquid crystalline liquid, and thus the flexible moiety may facilitate alignment of the mesogenic ligand with the surrounding liquid crystalline liquid. For instance, mesogenic ligands attached to a surface of a nanoparticle may align with the director of a surrounding liquid crystalline liquid (e.g., a nematic phase of the liquid crystalline liquid).

In certain embodiments, the mesogenic ligand has a phase transition temperature (also referred to as a melting temperature or clearing point) ranging from 50° C. to 150° C., such as 75° C. to 125° C., or 80° C. to 120° C., or 85° C. to 115° C., or 90° C. to 110° C. In certain embodiments, the mesogenic ligand has a phase transition temperature (e.g., melting temperature or clearing point) of 100° C. For example, the phase transition temperature may be a temperature at which the mesogenic ligand transitions from a first phase to a second phase (or vice versa). In some embodiments, the mesogenic ligand may transition from a phase having positional order (e.g., an ordered spatial arrangement of the ligands, such as in an ordered lattice) or directional order (e.g., alignment of the ligands along a common directional axis) to a phase having substantially no positional or directional order. In some embodiments, the mesogenic ligand may transition from a phase having substantially no positional or directional order to a phase having positional or directional order. In some cases, the mesogenic ligand has positional and/or directional order below the phase transition temperature, and substantially no positional or directional order above the phase transition temperature. Similarly, mesogenic ligands that are stably associated with or attached to a surface of mesogenic ligand-functionalized nanoparticles may have a phase transition from a phase having substantially no positional or directional order to a phase having positional or directional order (or vice versa). As described above, mesogenic ligands that are stably associated with or attached to a surface of mesogenic ligand-functionalized nanoparticles may have a phase transition temperature (also referred to as a melting temperature or clearing point) ranging from 50° C. to 150° C., such as 75° C. to 125° C., or 80° C. to 120° C., or 85° C. to 115° C., or 90° C. to 110° C. In certain embodiments, mesogenic ligands that are stably associated with or attached to a surface of mesogenic ligand-functionalized nanoparticles may have a phase transition temperature (e.g., melting temperature or clearing point) of 100° C.

In other embodiments, ligands suitable for functionalization of the nanoparticles are non-mesogenic ligands. In these embodiments, if the ligand is a non-mesogenic ligand, the functionalized nanoparticles may simply be referred to as ligand-functionalized nanoparticles. For instance, the ligand may be an organic compound. Examples of ligands that may be attached to a surface of the nanoparticle include, but are not limited to, octadecylamine (ODA), octadecylphosphonic acid, oleic acid, combinations thereof, and the like.

In certain embodiments, the ligand (e.g., mesogenic ligand) includes a cross-linkable functional group. The cross-linkable functional group may be a group that, when activated, can form an attachment to another moiety. In some cases, the attachment may attach a mesogenic ligand to another mesogenic ligand (e.g., a mesogenic ligand of an adjacent mesogenic ligand-functionalized nanoparticle), may attach a mesogenic ligand to a nanoparticle, may attach a mesogenic ligand to a ligand (e.g., a non-mesogenic ligand) of a ligand-functionalized nanoparticle (e.g., a non-mesogenic ligand-functionalized nanoparticle), may attached a ligand (e.g., a non-mesogenic ligand) to a mesogenic ligand (e.g., a mesogenic ligand of an adjacent mesogenic ligand-functionalized nanoparticle), or may attach a ligand (e.g., a non-mesogenic ligand) to another ligand (e.g., a ligand of an adjacent ligand-functionalized nanoparticle). In certain embodiments, the cross-linkable functional group forms a covalent bond attachment the other moiety. In certain embodiments, the cross-linkable functional group is a light activated cross-linkable functional group. A light activated cross-linkable functional group is a cross-linkable functional group that may form an attachment to another moiety when light is applied to the light activated cross-linkable functional group. For example, exposure of the light activated cross-linkable functional group to light may activate the functional group, thus forming a reactive moiety capable of forming a crosslink to another moiety as described above. In some instances, the applied light is ultraviolet (UV) light. In some instances, the applied light is visible light. In some instances, the applied light is infrared light. For example, the applied light may be UV light having a wavelength ranging from 100 nm to 400 nm, such as 150 nm to 400 nm, or 200 nm to 400 nm, or 300 nm to 400 nm. In some instances, the applied UV light may be approximately 350 nm, such as 360 nm or 364 nm. Other types of cross-linkable functional groups may also be used, such as chemically activated cross-linkable functional groups, and the like.

Any convenient cross-linkable functional group may be used. In certain embodiments, the cross-linkable functional group is a functional group that, when activated, forms a reactive moiety. The reactive moiety may then react with another moiety (e.g., ligand, mesogenic ligand, nanoparticle, etc.) to form an attachment (e.g., covalent bond) between the cross-linkable functional group and the other moiety. In some cases, the reactive moiety is a moiety capable of forming a covalent bond to carbon. For example, the reactive moiety may be a nitrene, such as a reactive nitrene derived from an azide functional group (e.g., an azide cross-linkable functional group). A nitrene may form a covalent bond to carbon to produce an amine or amide. In some instances, the cross-linkable functional group includes an azide, such as, but not limited to, a tetrafluoro-arylazide group.

In certain embodiments, the mesogenic ligand has a structure of formula (I):

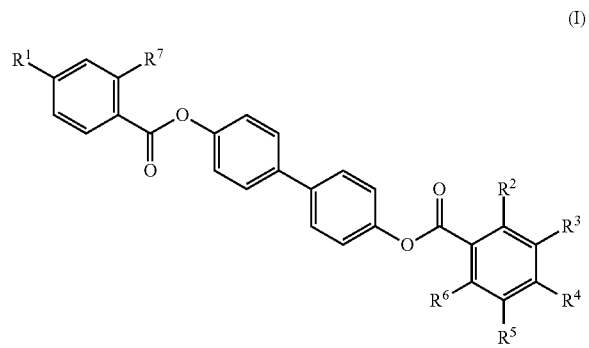

wherein $R^1$ to $R^7$ are each independently selected from H, halo, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, and substituted heteroaryl.

In some instances, $R^1$ to $R^7$ are each independently selected from H, halo, azido, alkyl, substituted alkyl, alkoxy, and substituted alkoxy.

In some instances, $R^1$ is alkoxy, such as a $C_{1-12}$ alkoxy, $C_{1-10}$ alkoxy, $C_{1-8}$ alkoxy, $C_{1-6}$ alkoxy, or $C_{1-3}$ alkoxy. In some instances, $R^1$ is $C_5$ alkoxy, such as pentyloxy. In some instances, $R^1$ is $C_8$ alkoxy, such as octyloxy.

In some instances, $R^2$ is H or halo. In some instances, $R^2$ is H. $R^2$ is halo, such as fluoro.

In some instances, $R^3$ is H or halo. In some instances, $R^3$ is H. $R^3$ is halo, such as fluoro.

In some instances, $R^5$ is H or halo. In some instances, $R^5$ is H. $R^2$ is halo, such as fluoro.

In some instances, $R^6$ is H or halo. In some instances, $R^6$ is H. $R^2$ is halo, such as fluoro.

In some instances, $R^4$ is alkoxy or azido. In some instances, $R^4$ is azido. In some instances, $R^4$ is alkoxy, such as a $C_{1-12}$ alkoxy, $C_{1-10}$ alkoxy, $C_{1-8}$ alkoxy, $C_{1-6}$ alkoxy, or $C_{1-3}$ alkoxy. In some instances, $R^4$ is methoxy. In some instances, $R^4$ is $C_3$ alkoxy, such as propoxy. In some instances, $R^4$ is $C_8$ alkoxy, such as octyloxy.

In some instances, $R^2$, $R^3$, $R^5$ and $R^6$ are each H. In some instances, when $R^2$, $R^3$, $R^5$ and $R^6$ are each H, $R^4$ is alkoxy.

In some instances, $R^2$, $R^3$, $R^5$ and $R^6$ are each halo, such as fluoro. In some instances, when $R^2$, $R^3$, $R^5$ and $R^6$ are each halo (e.g., fluoro), $R^4$ is azido. In some instances, $R^7$ is substituted alkoxy, such as a substituted $C_{1-12}$ alkoxy, substituted $C_{1-10}$ alkoxy, substituted $C_{1-8}$ alkoxy, substituted $C_{1-6}$ alkoxy, or substituted $C_{1-3}$ alkoxy. In some instances, $R^7$ is substituted $C_3$ alkoxy, such as substituted propoxy. In some instances, $R^7$ is substituted $C_6$ alkoxy, such as substituted hexyloxy. In some instances, the substituent on the substituted alkoxy is amino or substituted amino. In some instances, the substituent on the substituted alkoxy is amino, such that $R^7$ is aminoalkoxy, such as aminopropoxy (e.g., 3-aminopropoxy) or aminohexyloxy (e.g., 6-aminohexyloxy). In some embodiments, the mesogenic ligand is attached to a nanoparticle through the $R^7$ substituent. For instance, in embodiments where $R^7$ is an aminoalkoxy group, the mesogenic ligand may be attached to the nanoparticle through the amino group of the aminoalkoxy.

In certain embodiments, the mesogenic ligand has one of the following structures:

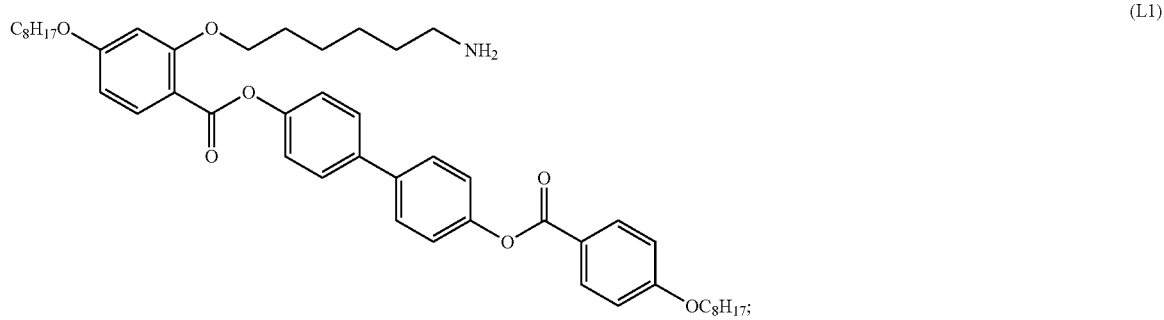

(L1)

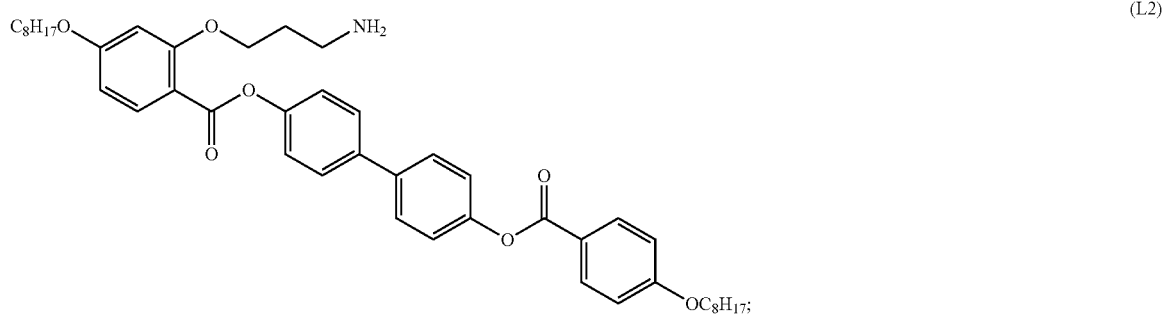

(L2)

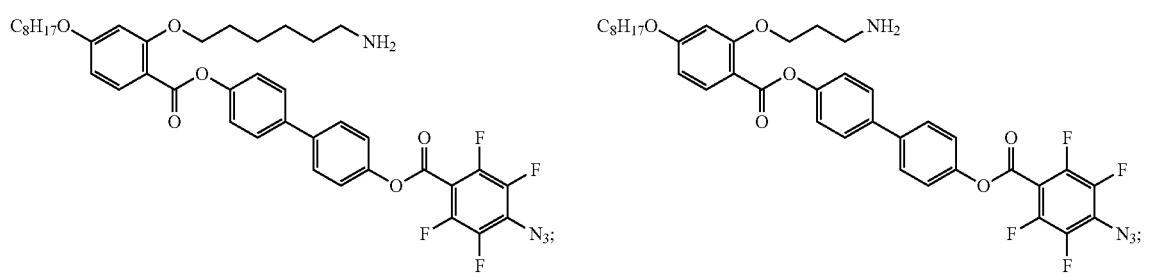

(L3) (L4)

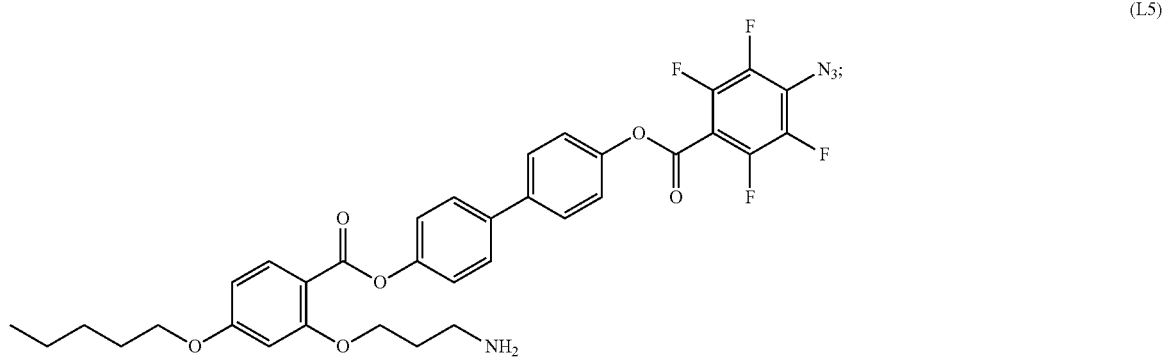

(L5)

-continued
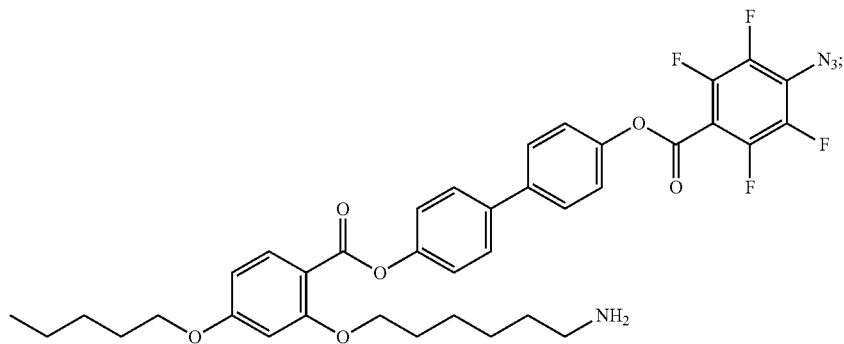
(L6)
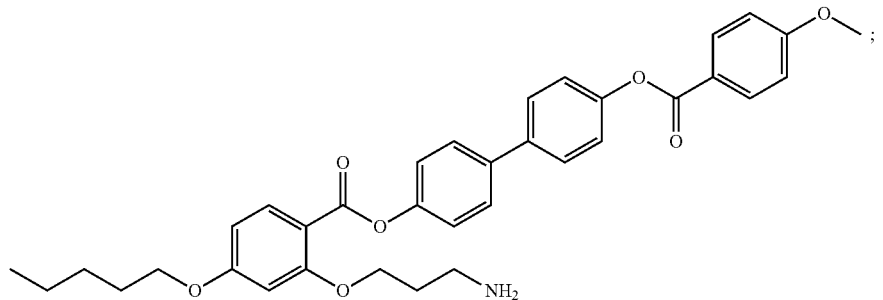
(L7)
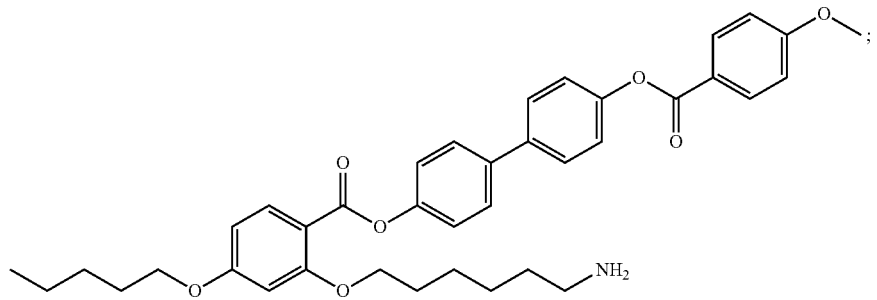
(L8)
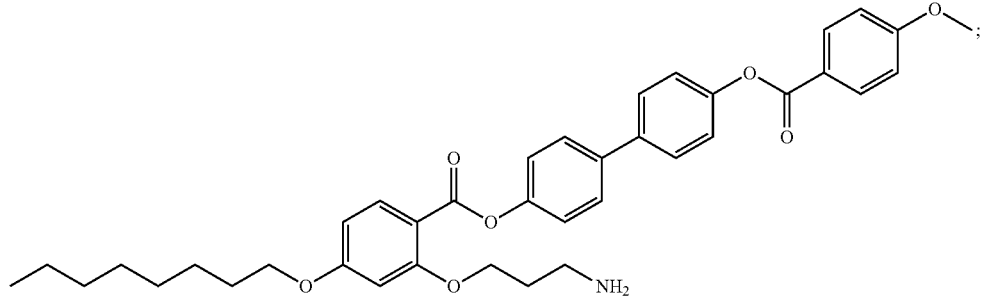
(L9)
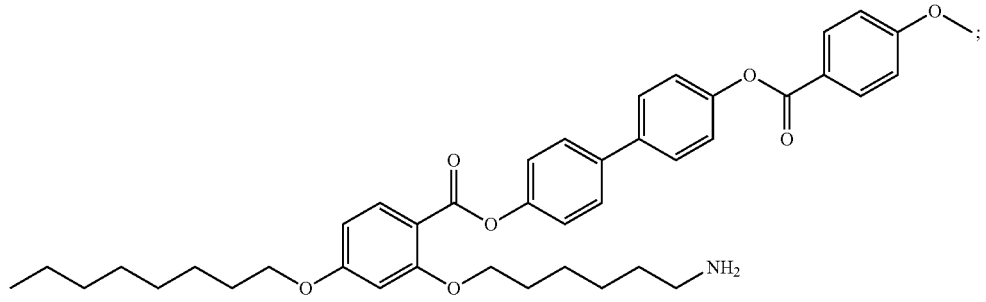
(L10)

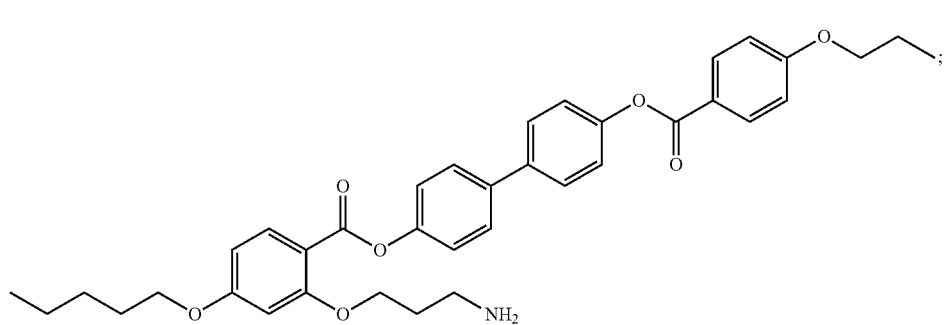
(L11)
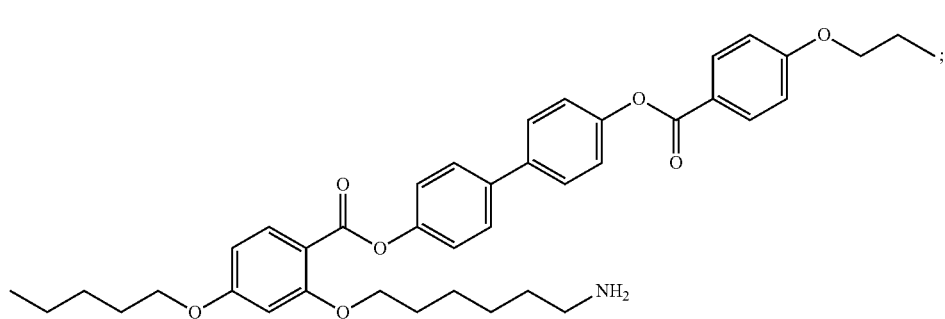
(L12)
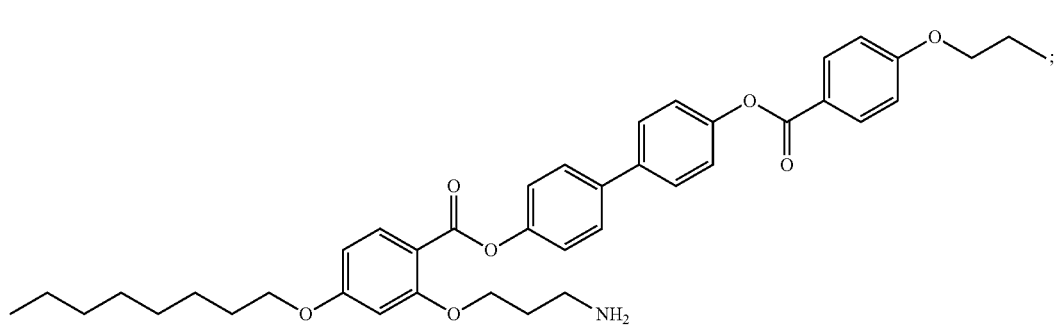
(L13)
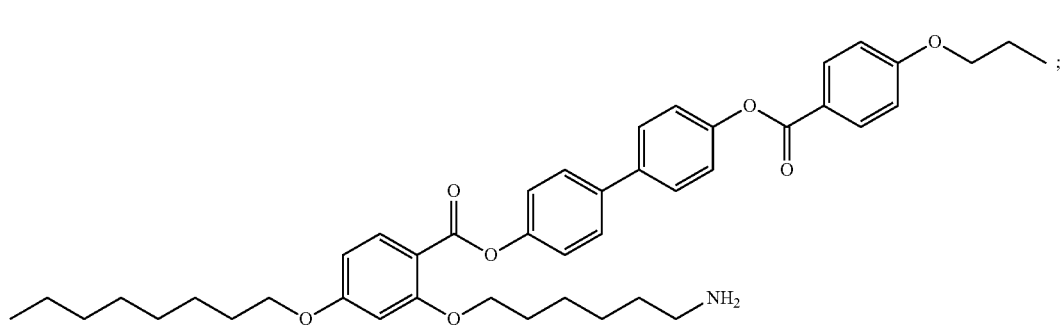
(L14)
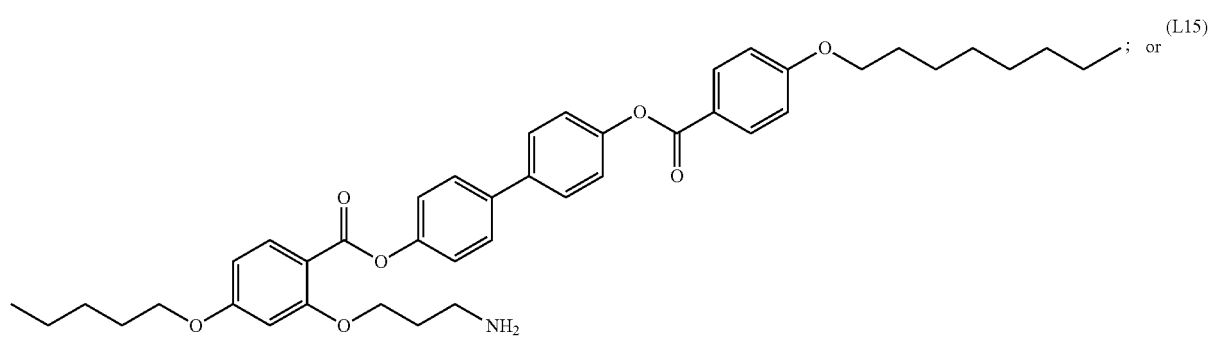
(L15)

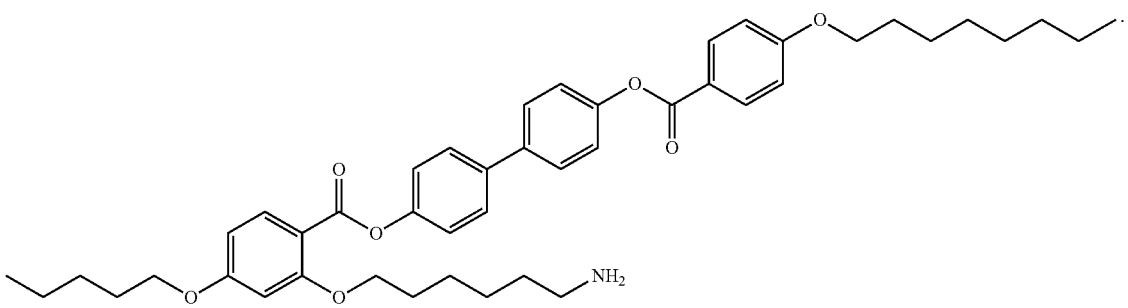
(L16)

As described above, the three-dimensional structures may be composed of nanoparticles having substantially the same physical and chemical characteristics, or in other embodiments, may be composed of nanoparticles having different physical and/or chemical characteristics. For example, physical and/or chemical characteristics of the nanoparticles that may be the same or may vary as described above may include, but are not limited to, size, shape, composition, ligand attached to the surface of the nanoparticle, mesogenic ligand attached to the surface of the nanoparticle, cross-linkable functional group, combinations thereof, and the like. For instance, a nanoparticle may include a plurality of ligands attached to the surface of the nanoparticle, where the ligands are substantially the same. In other instances, the nanoparticle may include a plurality of ligands attached to the surface of the nanoparticle, where the ligands are different (e.g., ligands having different chemical structures and/or functional groups, such as cross-linkable functional groups as described herein). For example, combinations of various ligands may be attached to the surface of the same nanoparticle.

Compositions

As described above, three-dimensional structures of the present disclosure may have a shell configuration that partially or completely encloses a space or material. In certain embodiments, the shell encloses a material, such as an active agent or an ink. In some instances, the active agent is a drug. Encapsulation of the active agent inside the three-dimensional structure may facilitate one or more of: delivery of the active agent to a desired site; formulation of the active agent into a desired formulation; increased stability of the active agent; controlled release of the active agent; delayed release of the active agent; and the like. Encapsulation of an ink inside the three-dimensional structure may facilitate one or more of: application of the ink to a surface of a substrate; tuning (e.g., changing, such as dynamically changing) the emission spectrum of the ink; and the like.

Three-dimensional structures of the present disclosure may also enclose other types of material, such as, but not limited to, a liquid crystal, a dye, an ink, combinations thereof, and the like. The liquid crystal enclosed by the three-dimensional structures may be a liquid crystal (e.g., a liquid crystal liquid) as described in more detail herein. For instance, the enclosed liquid crystal liquid may be a liquid crystal having a certain phase, such as, but not limited to, a liquid crystal in an isotropic phase, a liquid crystal in a nematic phase, a liquid crystal in a cholesteric phase, and the like. A liquid crystal in a cholesteric phase may also be referred to a liquid crystal in a chiral nematic phase. Liquid crystals in a cholesteric (chiral nematic) phase exhibit a twisting of the liquid crystal molecules perpendicular to the director, with the molecular axis of the liquid crystals parallel to the director.

Aspects of the present disclosure include compositions that include the three-dimensional structures as disclosed herein. The composition may include the three-dimensional structure and a liquid. In some instances, the composition includes the three-dimensional structure dispersed in the liquid. In some instances, the liquid is a liquid crystalline fluid (e.g., a liquid crystalline liquid), such as a liquid crystalline liquid as described in more detail below. In some instances, the liquid is a solvent. Any convenient solvent may be used, depending on the desired composition of three-dimensional structures. Examples of solvents include, but are not limited to, organic solvents, such as toluene, dimethylbenzene, methylisopropylbenzene, methanol, ethyl acetate, chloroform, mixtures thereof, and the like. In some instances, the solvent is toluene.

Aspects of the present disclosure also include compositions for producing a three-dimensional structure of stably associated mesogenic ligand-functionalized nanoparticles described herein. In certain embodiments, the composition includes nanoparticles and a liquid crystalline fluid (e.g., a liquid crystalline liquid). The nanoparticles in the composition for producing the three-dimensional structures may be any of the nanoparticles as described herein. For instance, the nanoparticles may be ligand-functionalized nanoparticles, such as mesogenic ligand-functionalized nanoparticles as described herein.

In certain cases, the composition includes a liquid crystalline fluid (e.g., a liquid crystalline liquid). The liquid crystalline fluid may be composed of a liquid crystal. In certain cases, the liquid crystal has a phase transition, such as a phase transition between an isotropic phase and a nematic phase (or vice versa). By "isotropic phase" or "isotropic" is meant a liquid crystal phase where the liquid crystals have no significant positional order or directional order. By "nematic phase" or "nematic" is meant a liquid crystal phase where the liquid crystals have no significant positional order, but have a detectable directional order. In some instances, the liquid crystal phase transition occurs in response to a stimulus applied to the liquid crystals. The stimulus may be any convenient stimulus that can induce a phase transition in the liquid crystals, such as, but not limited to, a change in temperature, an electrical stimulus, a magnetic stimulus, combinations thereof, and the like. In some cases, the stimulus that induces the phase transition in the liquid crystal is a change in temperature, e.g., heating or cooling. As such, the liquid crystalline fluid may be composed of a liquid crystal that has a temperature dependent phase transition. In some embodiments, the liquid crystalline fluid undergoes a phase transition from an isotropic phase to a nematic phase when the temperature of the liquid crystalline fluid is reduced to below the phase transition temperature. In some embodiments, the liquid crystalline fluid undergoes a phase transition from a nematic phase to an isotropic phase when the temperature of the liquid crystalline fluid is increased to above the phase transition temperature.

In certain embodiments, a temperature dependent liquid crystalline fluid has a phase transition temperature that is lower than the phase transition temperature of a mesogenic ligand (or a mesogenic ligand-functionalized nanoparticle) as described herein. As such, in some instances, the phase transition temperature (e.g., melting temperature or clearing point) of the mesogenic ligand (or mesogenic ligand-functionalized nanoparticle) is greater than the phase transition temperature of the liquid crystalline fluid. In certain instances, a temperature dependent liquid crystalline fluid has a phase transition temperature (e.g., for a phase transition between an isotropic phase and a nematic phase) ranging from 20° C. to 50° C., such as 25° C. to 45° C., or 30° C. to 40° C. In some cases, a temperature dependent liquid crystalline fluid has a phase transition temperature (e.g., for a phase transition between an isotropic phase and a nematic phase) of approximately 35° C., such as 34° C. Examples of liquid crystalline fluids that have a temperature dependent phase transition include, but are not limited to, 4-cyano-4'-pentylbiphenyl (5CB), and the like.

Methods

Aspects of the present disclosure include methods of producing a three-dimensional structure of stably associated mesogenic ligand-functionalized nanoparticles described herein. The method of producing the three-dimensional structures includes dispersing the nanoparticles in a liquid crystalline fluid (e.g., a liquid crystalline liquid). The nanoparticles used in the methods for producing the three-dimensional structures may be any of the nanoparticles as described herein. For instance, the nanoparticles may be ligand-functionalized nanoparticles, such as mesogenic ligand-functionalized nanoparticles as described herein.

The nanoparticles may be dispersed in the liquid crystalline fluid using any convenient method, such as, but not limited to, mixing, vortexing, shaking, applying sound energy (also referred to as "sonication" herein), combinations thereof, and the like. In some cases, the method includes applying sound energy to the nanoparticles in the liquid crystalline fluid to disperse the nanoparticles in the liquid crystalline fluid. The nanoparticles may be dispersed in the liquid crystalline fluid such that the nanoparticles are substantially evenly distributed throughout the liquid crystalline fluid. For example, a mixture of the nanoparticles and liquid crystalline liquid may be substantially homogeneous. In certain embodiments, the nanoparticles are dispersed in the liquid crystalline fluid at room temperature (e.g., ~25° C.). In other cases, the nanoparticles are dispersed in the liquid crystalline fluid at a temperature other than room temperature, e.g., lower or higher than room temperature. In some instances, the nanoparticles are dispersed in the liquid crystalline fluid at a temperature higher than room temperature. In certain embodiments, the nanoparticles are dispersed in the liquid crystalline fluid at a temperature where the nanoparticles are present in a desired phase of the liquid crystalline fluid, such as an isotropic phase or a nematic phase. For instance, embodiments of the methods include dispersing the nanoparticles in the liquid crystalline fluid at a temperature where the nanoparticles are present in an isotropic phase of the liquid crystalline fluid. In certain aspects, the temperature where the nanoparticles are present in an isotropic phase of the liquid crystalline fluid is a temperature above the phase transition temperature of the liquid crystalline fluid, such as a temperature ranging from 20° C. to 50° C., such as 25° C. to 45° C., or 30° C. to 40° C., such as a temperature of approximately 35° C., for example 34° C.

Embodiments of the method of producing the three-dimensional structures described herein also include inducing a phase transition in the liquid crystalline fluid (e.g., the liquid crystalline liquid) to produce the three-dimensional structure. In certain embodiments, the phase transition of the liquid crystalline liquid is a phase transition from an isotropic phase to a nematic phase. Thus, the method may include inducing a phase transition from an isotropic phase to a nematic phase in the liquid crystalline liquid.

In some instances, inducing a phase transition in the liquid crystalline liquid is performed by applying a stimulus to the liquid crystalline liquid. The stimulus may be any convenient stimulus that can induce a phase transition in the liquid crystals, such as, but not limited to, a change in temperature, an electrical stimulus, a magnetic stimulus, combinations thereof, and the like. In some cases, inducing the phase transition in the liquid crystalline liquid is accomplished by changing the temperature of the liquid crystalline liquid, e.g., heating or cooling the liquid crystalline liquid. In certain instances, inducing the phase transition in the liquid crystalline liquid is accomplished by decreasing the temperature of the liquid crystalline liquid to a temperature below the phase transition temperature of the liquid crystalline liquid. Reducing the temperature of the liquid crystalline liquid to a temperature below the phase transition temperature of the liquid crystalline liquid may induce a phase transition of the liquid crystalline liquid from an isotropic phase to a nematic phase. In some cases, at the isotropic to nematic phase transition in a homogeneous liquid crystalline liquid, domains of nematic ordering form and grow as the liquid crystalline liquid is cooled through the transition temperature. As the nematic domains form and increase in size, isotropic domains began decreasing in size. In some instances, the dispersed nanoparticles (e.g., mesogenic ligand-functionalized nanoparticles) in the liquid crystalline liquid may preferentially locate in the shrinking isotropic domains. As the nanoparticles aggregate at the interface between the isotropic and nematic domains, the nanoparticles may form a three-dimensional structure of stably associated nanoparticles as described herein. For example, a three-dimensional structure having a shell configuration may be produced, such as a shell configuration having a spherical surface.

As described above, in certain embodiments, the functionalized nanoparticles may include a mesogenic ligand having a cross-linkable functional group. As such, embodiments of the method may further include crosslinking the mesogenic ligand-functionalized nanoparticles in the three-dimensional structure. For instance, after the formation of the three-dimensional structure, the cross-linkable functional group may be activated by applying an appropriate stimulus to the cross-linkable functional group of the nanoparticle. In certain embodiments, the cross-linkable functional group is a light activated cross-linkable functional group. As such, certain embodiments of the methods include applying light to the light activated cross-linkable functional group sufficient to activate crosslinking of the light activated cross-linkable functional group. Where the light activated cross-linkable functional group is activated by UV light, the method includes applying ultraviolet (UV) light. For example, the method may include applying UV light having a wavelength ranging from 100 nm to 400 nm, such as 150 nm to 400 nm, or 200 nm to 400 nm, or 300 nm to 400 nm. In some instances, the method includes applying UV light having a wavelength of approximately 350 nm, or 360 nm or 364 nm. In other embodiments, the stimulus applied to the cross-linkable functional group may include visible light, infrared light, a chemical stimulus, combinations thereof, etc.

Aspects of the method of producing the three-dimensional structures may further include separating the produced three-dimensional structures from the liquid crystalline fluid (e.g., liquid crystalline liquid) used to produce the three-dimensional structures.

Any convenient separation method may be used to separate the three-dimensional structures from the liquid crystalline liquid. For example, the separation method may include filtering, centrifuging, chromatography, extraction, and the like. In some instances, separating the three-dimensional structures includes adding the produced three-dimensional structures to a solvent. The solvent used may added in a large excess volume as compared to the volume of liquid crystalline liquid used to produce the three-dimensional structures to substantially disperse the liquid crystalline liquid. Examples of solvents include, but are not limited to, organic solvents, such as toluene, dimethylbenzene, methylisopropylbenzene, methanol, ethyl acetate, chloroform, mixtures thereof, and the like. In some instances, the solvent is toluene.

Utility

The subject structures, compositions and methods find use in a variety of different applications where three-dimensional microstructures, such as three-dimensional microstructures having a shell configuration (e.g., microshells), are desired. For example, the three-dimensional microstructures, compositions and methods find use in light emitting devices, such as, but not limited to, light emitting devices that are components of video displays, lights, etc. In these embodiments, the three-dimensional microstructures may be provided on a surface of a substrate. For instance, the three-dimensional microstructures may be disposed on a surface of the substrate, such as arranged as a layer of three-dimensional microstructures on a surface of the substrate. The substrate may be any desired type of substrate that is suitable for use in a light emitting device, such as, but not limited to, a substrate for an integrated circuit or a substrate for a microelectricalmechanical system (MEMS) device, etc. (e.g., a silicon substrate).

In certain embodiments, the light emitting device is a component of a light, such as a light emitting diode (LED). As described above, the three-dimensional microstructures include nanoparticles, such as quantum dots, and as such, the light emitting device may be a component of a quantum dot LED (QD-LED). In some cases, using the three-dimensional microstructures disclosed herein in an LED may facilitate an increase in the possible color spectrum of the LED. For instance, the emission spectrum of the LED may depend on the size of the three-dimensional microstructures, and as such, the emission color of the LED may be tuned depending on the size of the three-dimensional microstructures. In some embodiments, the three-dimensional microstructures may be used as a coating on a surface of a conventional LED (e.g., a QD coating). Light emitted from the conventional LED may photo-excite the QD coating, thus causing the three-dimensional microstructures in the QD coating to emit light of a different wavelength.

In other embodiments, the three-dimensional microstructures may emit light via direct electrical excitation. For example, an electric field may be applied to the three-dimensional microstructures (e.g., QD microstructures), thus causing emission of light from the three-dimensional microstructures.

In some instances, the light emitting device is a component of a video display. As described above, the three-dimensional microstructures include nanoparticles, such as quantum dots, and as such, the light emitting device may be a component of a quantum dot video display. In some cases, the quantum dot video display may include the three-dimensional microstructures of the present disclosure as a filter for conventional LEDs. For example, as described above, light emitted from a conventional LED may photo-excite the QD-containing three-dimensional microstructures, thus causing the three-dimensional microstructures to emit light of a different wavelength. In other embodiments, the quantum dot video display may include the three-dimensional microstructures of the present disclosure, where the three-dimensional microstructures emit light via direct electrical excitation, as described above. In certain embodiments, quantum dot-containing three-dimensional microstructures are characterized by pure and saturated emission colors with narrow bandwidth, and thus may facilitate production of a QD video display that has high color purity and efficiency, as compared to conventional LED or OLED video displays.

As described above, in certain instances, the spacing between adjacent nanoparticles is selected so as to minimize shifts in the emission spectrum of the nanoparticles. As such, the three-dimensional structures of the present disclosure find use in facilitating the production of light emitting devices that have pure and saturated emission colors with narrow bandwidth as described above. In addition, in certain instances, the spacing between adjacent nanoparticles is selected so as to minimize energy losses due to fluorescence resonance energy transfer (FRET). As such, the three-dimensional structures of the present disclosure find use in facilitating the production of light emitting devices that are more efficient as compared to conventional light emitting devices.

Three-dimensional microstructures of the present disclosure also find use in applications such as the encapsulation of an ink. Encapsulation of an ink inside the three-dimensional structure may facilitate one or more of: application of the ink to a surface of a substrate; tuning (e.g., changing, such as dynamically changing) the emission spectrum of the ink; and the like. For example, encapsulation of an ink in a three-dimensional structure of the present disclosure may be used to produce a light activated ink, such as a laser light activated ink. Exposure of the light activated ink to a light source (e.g., a laser) may photo-excite the three-dimensional microstructures (e.g., QD-containing three-dimensional microstructures), thus causing the three-dimensional microstructures to emit light.

Three-dimensional microstructures (e.g., microshells) of the present disclosure also find use in applications such as the encapsulation of active agents. Encapsulation of the active agent inside the microshells may facilitate one or more of: delivery of the active agent to a desired site; formulation of the active agent into a desired formulation; increased stability of the active agent; controlled release of the active agent; delayed release of the active agent; and the like.

Three-dimensional microstructures, compositions and methods of the present disclosure also find use in applications such as optical imaging. For instance, three-dimensional microstructures find use as probes for optical imaging, contrast agents, or as detectable labels for labeling biological tissues. In some instances, the three-dimensional microstructures, compositions and methods of the present disclosure find use in optical imaging applications where dynamic control of the optical properties of the three-dimensional microstructures is desired, such as by applying a physical, electrical, magnetic, etc. stimulus to the three-dimensional microstructures to alter the optical properties of the mesogenic ligands.

Kits

Aspects of the present disclosure additionally include kits that include three-dimensional structures as described in detail herein. In some instances, the kit includes a packaging for containing the three-dimensional structures. In certain embodiments, the packaging may be a sealed packaging, e.g., in a water vapor-resistant container, optionally under an air-tight and/or vacuum seal. In certain instances, the packaging is a sterile packaging, configured to maintain the three-dimensional structures enclosed in the packaging in a sterile environment. By "sterile" is meant that there are substantially no microbes (such as fungi, bacteria, viruses, spore forms, etc.). The kits may further include a fluid (e.g., a liquid). For instance, the kit may include a liquid, such as a liquid in which the three-dimensional structures are provided. For example, the three-dimensional structures may be dispersed in the liquid. Liquids in which the three-dimensional structures may be dispersed include, but are not limited to, a liquid crystalline fluid (e.g., liquid crystalline liquid), a solvent (e.g., an organic solvent such as toluene, dimethylbenzene, methylisopropylbenzene, etc.), and the like.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., CD, DVD, Blu-Ray, computer-readable memory (e.g., flash memory), etc., on which the information has been recorded or stored. Yet another means that may be present is a website address which may be used via the Internet to access the information at a removed site. Any convenient means may be present in the kits.

As can be appreciated from the disclosure provided above, embodiments of the present invention have a wide variety of applications. Accordingly, the examples presented herein are offered for illustration purposes and are not intended to be construed as a limitation on the invention in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by mass, molecular mass is mass average molecular mass, temperature is in degrees Celsius, and pressure is at or near atmospheric.

EXAMPLES

Example 1

The mesogenic ligands used in this example are shown in FIG. 1. The ligand molecules contained a rigid aromatic core region surrounded by flexible domains at the termini, which gave the ligand the ability to interact with the host liquid crystal matrix to produce a uniform dispersion. The ligands were divided into two classes; the mesogenic ligands (ligands L1 and L2) and the crosslinkable mesogenic ligands (ligands L3 and L4), each containing a varying length in the alkyl amine side-arm, which attached the ligand to the particle surface. The ligands exhibited liquid crystalline phases in their pure state with high clearing points above 100° C.—a contrast with the host phase (5CB (4-Cyano-4'-pentylbiphenyl)), which exhibited the nematic to isotropic transition at 34° C.).

Ligands were attached (also referred to herein as "exchanged") on to the surface of CdSe quantum dots (5.2-6.2 nm, NN Labs Inc.) to form LC-QDs. These particles were then dispersed into a nematic liquid crystal, 5CB by wt %. Bath sonication for eight hours at 40° C. in the isotropic phase dispersed the particles, as verified by fluorescence microscopy.

Once a homogenous suspension was obtained, nanoparticle shell formation was initiated by a fast cooling stage. As the composite material was cooled into the nematic phase by immediate transfer from a 40° C. heating block to a second temperature stage, at 30° C., the system phase-separated into LC-QD rich droplets in an LC-QD poor (5CB rich) host phase. During this stage of the process, the functionalized QDs partitioned into shrinking isotropic domains mainly due to elastic forces. After a period of time, a dense spherical wall of QDs was observed to form and no further shrinkage was observed. As the isotropic domains, rich in LC-QDs, shrunk, they gathered nanoparticles, concentrating them at the shrinking interface. This behavior was observed if the timescale of droplet formation was faster than the timescale required for uniform Brownian particle dispersion within the droplet. At high concentration at the droplet inter-face, the particles interacted and packed densely, forming the solid shell.

Figure 2:
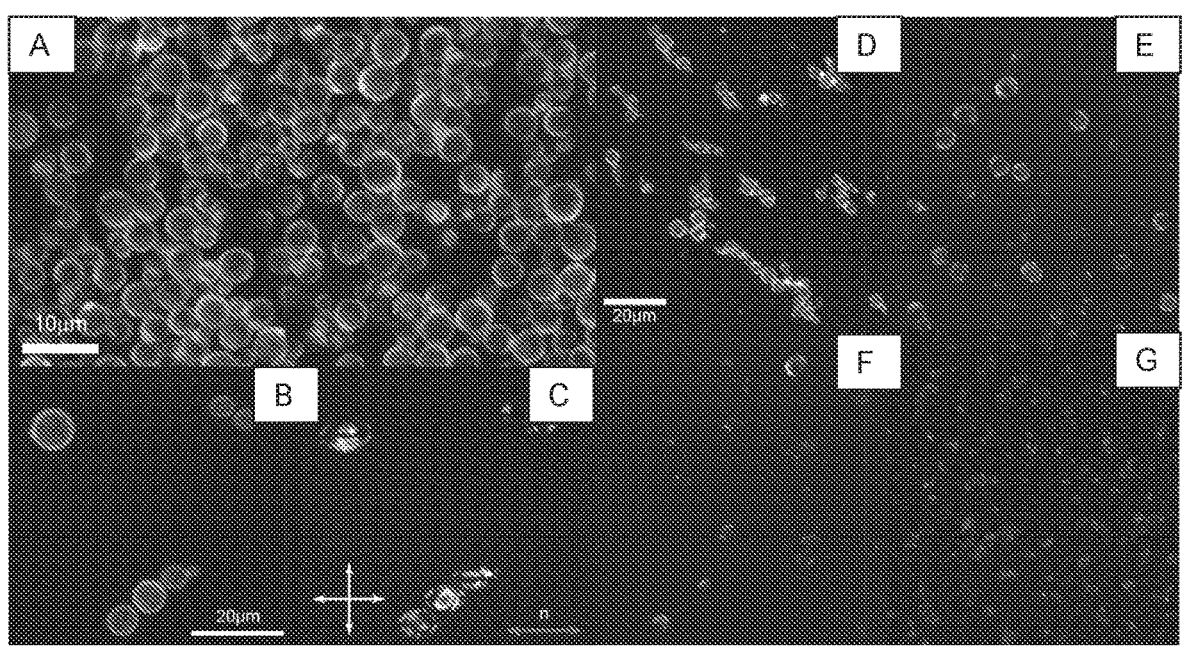
FIG. 2, panel A, shows a fluorescence microscopy image of nanoparticle (e.g., quantum dot, QD) shells formed from 620 nm CdSe—ZnS QDs, functionalized with ligand L1 suspended in nematic liquid crystal at room temperature.

By varying initial QD concentration in the nematic host, shell size could be controlled as each shell contained QDs swept up from a local volume. At low overall LC-QD concentrations (~0.1 wt %), micron-sized droplets formed, which may be very small shells. Concentrations ranging from 0.1 to 0.5 wt % yielded well defined shells as seen in FIG. 2. Higher concentrations produced increasing amounts of QDs found out-side of the shell. The formation process was carried out on a microscope slide, or alternately produced a large number of shells when carried out in bulk (e.g., using a 1 ml Eppendorf tube). After formation, the shells were pipetted out or centrifuged to concentrate at the bottom of the tube without noticeable damage or de-formation.

Fluorescence microscopy was used to track QD organization throughout the transition and therefore elucidate the shell formation process. FIG. 2, panel B, and FIG. 2, panel C, show corresponding fluorescence and birefringence images of a few shells. In FIG. 2, panel C, the host nematic phase appeared dark because the nematic director, n, was oriented parallel with one of the crossed polarizer directions (indicated by the white arrows). This image shows the birefringence of the shell interior (an area depleted of fluorescent QDs) and the topological defects surrounding the shells. Colloidal particles with a radial ligand distribution producing either homeotropic or planar surface anchoring conditions created characteristic topological defects when surrounded by the nematic phase. Such defects were visualized with optical microscopy, providing information on ligand organization at the particle surface. The presence of horizontal Saturn ring defects around some shells in FIG. 2, panel C, indicated that the outer ligands were aligned parallel to the shell surface, producing a planar surface anchoring condition. In addition, bipolar-type defects were also observed as expected for this geometry. In this image, the surrounding 5CB material was aligned using a standard rubbed polyvinyl alcohol (PVA) alignment layer for optimal defect visualization. Detailed observations of a large number of shells revealed that they consistently appear to exhibit planar surface anchoring and defects representative of a vertical surface alignment were not seen.

Three-dimensional structures (e.g., shell structures as described herein) using QD nanoparticles exchanged with ligands L1, L1, L3 and L4, respectively, were prepared according to the procedures described herein.

Temperature and Mechanical Stability

Two different versions of the QD shells were tested for temperature stability, using ligands L1 and L2. In both cases shell structures were very robust to temperature change and appeared quite rigid when dispersed in the liquid crystal phase. On reheating the system to the liquid crystal isotropic point, no noticeable shape changes were observed in the shells despite significant flow of the surrounding liquid crystal. At the transition point, where isotropic domains began to nucleate in the host phase, the already formed shells moved into those domains and clustered. The micronscale size of these shells indicated that elastic forces dominated this process.

Once formed, the shells were very stable in 5CB. After heating above the liquid crystal isotropic point (34° C.) the shells for both tested ligands continued to maintain a rigid spherical structure on slow heating (1°/min), as indicated by observation of the tumbling motion of some shells with surface imperfections in the melted (isotropic) 5CB. No thermal shape fluctuations were observed up to more than 110° C. and the shells moved freely around the microscope slide without bursting, deforming or fusing with each other or the glass surface.

At higher temperatures fragmentation was observed and the QDs re-dispersed into the surrounding material. FIG. 2 illustrates this process for ligand L2. In this case, when observed on a microscope slide, the shells started to break apart at 115° C. (FIG. 2, panel E). Complete re-dispersion took place over a fairly broad temperature range (~10° C.). The process was somewhat reversible and after heating the material to a uniform state at 125° C., the shells were subsequently reformed by an additional rapid cooling step to produce smaller shell structures. The smaller size of these "secondary" shells may be due to incomplete re-dispersion. This would overall reduce the typical concentration in a given volume, therefore producing smaller shells. The observed shell 'melting' temperature for each ligand tested was far above the clearing point of pure 5CB and closer to that of the pure ligand. These observations indicated that, once formed, the elastic forces that governed the self-assembly process were no longer important for maintaining shell stability. Instead, local interactions between ligand molecules in the shell provided the driving force for stabilization.

Structural Characterization Experiments were performed for structural characterization of the system using small angle x-ray diffraction (SAXS) and transmission electron microscopy (TEM).

As a comparison, SAXS and TEM on nanoparticle clusters in the nematic phase using ODA ligands indicated aggregates with a fractal-like, disordered structure. For the structures according to embodiments of the present disclosure, TEM confirmed the hollow vesicle-like shell morphology and revealed the shell wall to be a dense, randomly packed assembly of the nanoparticles (FIG. 3, panels A-C).

Nanoparticle packing in the QD-LC-ligand shells was quantified using SAXS, varying QD concentration and ligand type. The scattering patterns shown in FIG. 3 showed a broad unoriented peak (A), at q=0.0616 (FIG. 3, panel D). Å-1 represented a real-space distance of 10.20 nm and was assumed to correspond to the average spacing between quantum dots in the shell wall. This number matched the expected separation of QDs shielded by bulky mesogenic ligands and was consistent with inter-particle separations in disordered aggregates of QDs functionalized with ligand L1. Peak A was fairly broad, indicative of a relatively disordered particle packing and consistent with the TEM observations and calculated FFT (FIG. 3, panels A-C).

Figure 3:
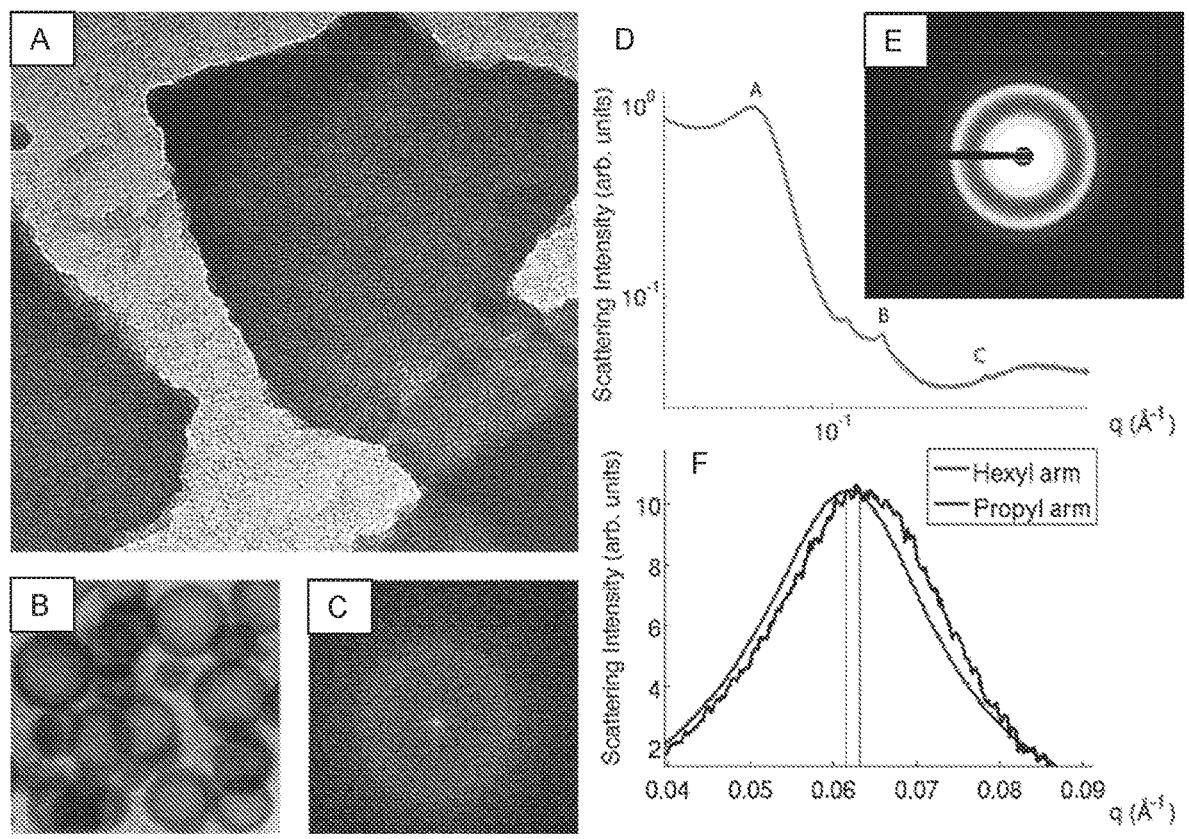
FIG. 3 shows transmission electron microscopy images of QD shells.

QDs functionalized with ligand L2 bearing a shorter connecting arm, produced a slight shift in peak A (FIG. 3, panel F). This new position corresponded to a QD spacing of 9.94 nm, compared to 10.20 nm for the longer connecting arm of ligand L1. This decrease in particle spacing was consistent with the shorter ligand-particle standoff distance as a result of the three carbon truncation in the amine containing chain, thus reducing the average particle separation within the shells.

The diffraction pattern also showed the sharp polycrystalline ring at position B, at 0.128 Å$^{-1}$, also visible as sharp spots on the CCD image (FIG. 3, panel E). This peak was indicative of a relatively well-defined crystalline structure of length scale 4.9 nm. This d-spacing, while too small to correspond to an inter-nanoparticle separation, matched the end-to-end dimensions of the ligand molecule rigid core. This result and general observations of the mechanical rigidity of the shell walls indicated that this sharp peak originated from local ligand crystallization within the shell wall. As the LC-QDs were concentrated at the droplet interface during formation, they may become stabilized by ligand-ligand interactions at a particular drop size. This droplet size in turn was dependent on the initial concentration of the composite.

Figure 4:
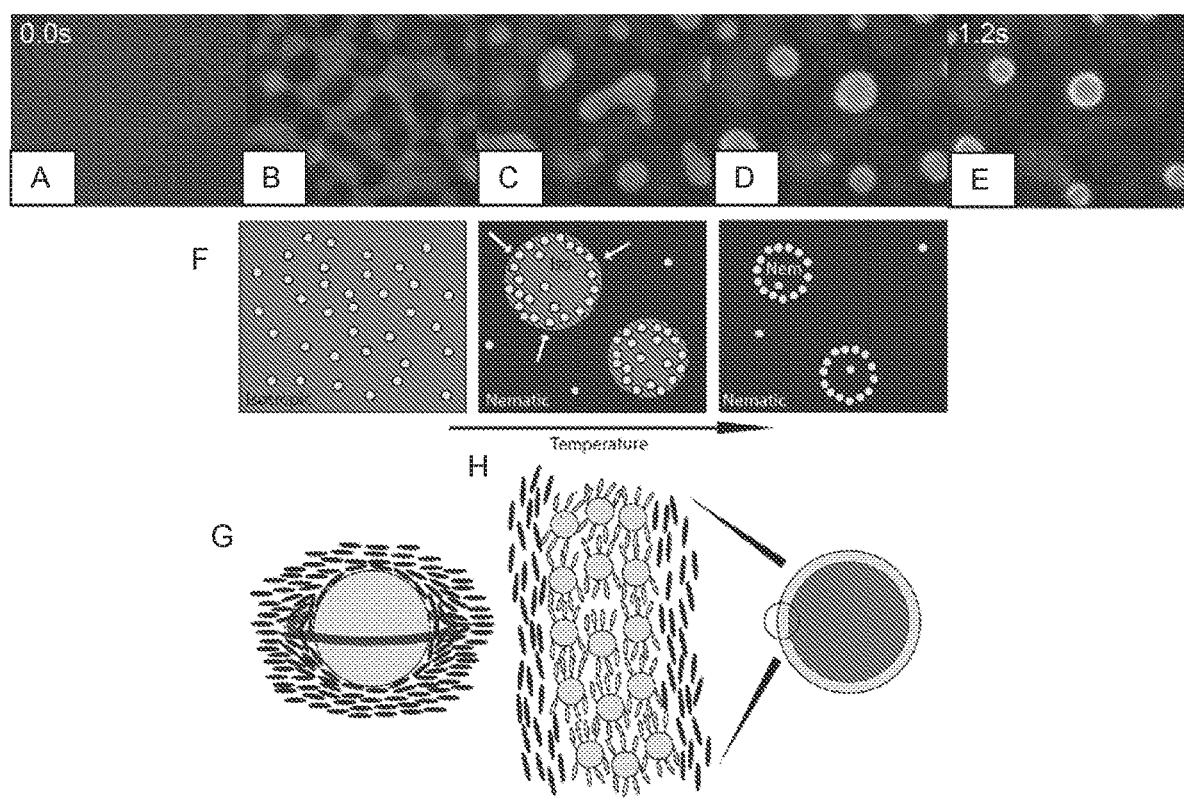
FIG. 4, panels A-E, show images from a high speed fluorescence video demonstrating the nanoparticle shell formation process by visualizing QD distribution over 1.2 s. Image width=60 µm.

FIG. 4, panels A-E, show several fluorescence microscopy images of the formation process, showing QD segregation, droplet formation and wall thickening. The isotropic to nematic phase transition acted as a template for QD assembly at the phase boundary. FIG. 4, panel F, shows a schematic of the fast formation mechanism. FIG. 4, panel G and FIG. 4, panel H, show schematics of the shell structure. The shell walls were composed of a densely packed assembly of functionalized particles, stabilized by ligand-ligand interactions. The surface of the shell structure adopted a planar surface-anchoring configuration as deduced from defect arrangements in the surrounding nematic phase.

Ligand Cross-linking and Shell Extraction

Having confirmed that the relatively robust QD shells were stable to temperatures up to ~120° C. in the host LC material, experiments were performed to determine if the shells could be removed from the host liquid crystal material and resuspended in different solvents. Achieving this step may facilitate potential applications for the assemblies. The LC host material 5CB was a viscous fluid with distinct optical properties. Redispersing the assemblies in an organic solvent such as toluene allowed them to be processed for use in a variety of coatings and solution-based formulations.

To achieve crosslinking, the shells were first formed as described above, but using the UV cross-linkable ligands L3 and L4, which incorporated an electron poor aryl azide in place of the distal benzoic acid moiety. A tetrafluoro-arylazide group was used, which acted as an efficient nitrene precursor with a high insertion efficiency.

Figure 5:
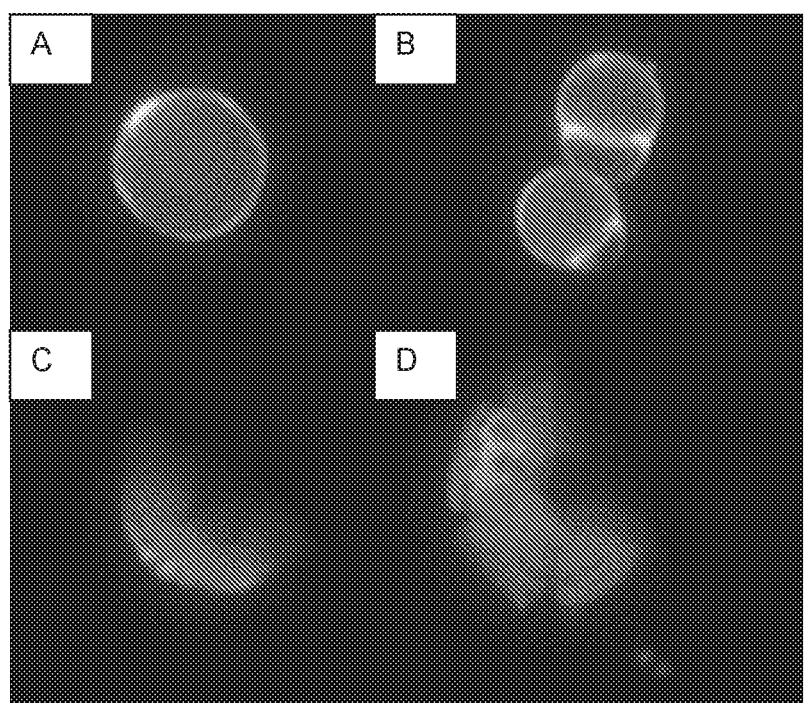
FIG. 5 shows fluorescence microscopy images of cross-linked QD shells formed from ligand L3 (FIG. 5, panel A).

To demonstrate that the shells could be extracted from the liquid crystal host and re-dispersed in a different solvent, shells were formed in bulk cooling the host phase from isotropic to nematic as described above. The material was then exposed to a 6.4 mW/cm$^2$ UV lamp (364 nm) for 1.5 hrs. Some shells were pipetted from the bulk after formation and diluted in a larger volume of toluene, effectively removing the nematic phase. This toluene mixture was then placed on a microscope slide and the shells imaged via fluorescence microscopy as the toluene slowly evaporated. Intact spherical shell structures were still present after the toluene dilution step (FIG. 5, panel A, and FIG. 5, panel B), indicating that they were robust enough to be extracted for applications. After solvent evaporation, the dry shells tended to split, but still maintained their solid-wall structure (FIG. 5, panel C, and FIG. 5, panel D), further demonstrating their structural integrity.

Conclusions

Methods for the formation of self-assembled nanoparticle micro-shells were tested. The structures were templated at the isotropic to nematic phase boundary in a liquid crystal host material using a process mediated by tunable mesogenic surface ligands.

Chemical control of shell size and structure was achieved by varying NP concentration and connecting ligand design. Since these parameters were independent of particle type, the process may be used with any appropriately sized NPs or combinations thereof, including mixtures of metallic, semiconducting and magnetic particles. This method may facilitate the creation of non-planar 3D nano-assemblies, templated by the geometry of different liquid crystal phase transitions, and may be used to generate customizable capsules for photonics and condensed matter applications or bio-molecular encapsulation.

Example 2

General

Solvents and chemicals were obtained from commercial sources (Aldrich, TCI-America, AK-Scientific and Acros) and used as received. $^1$H and $^{13}$C NMR spectra were recorded on either a Bruker DRX-600 equipped with a DCH cryoprobe or a Bruker DRX-500. Chemical shifts (δ) are expressed in parts per million relative to residual CHCl$_3$ or H$_2$O as internal standards. Proton magnetic resonance ($^1$H NMR) spectra were recorded at either 600 MHz or 500 MHz. Carbon magnetic resonance ($^{13}$C NMR) spectra were recorded at 150 MHz or 125 MHz. NMR acquisitions were performed at 295 K unless otherwise noted. Abbreviations are: s, singlet; d, doublet; t, triplet; q, quartet; br s, broad singlet. TLC analysis was performed using precoated silica gel 60 F$_{254}$ plated from EMD Chemicals Inc.

Synthesis of Mesogenic Ligands

General Procedure

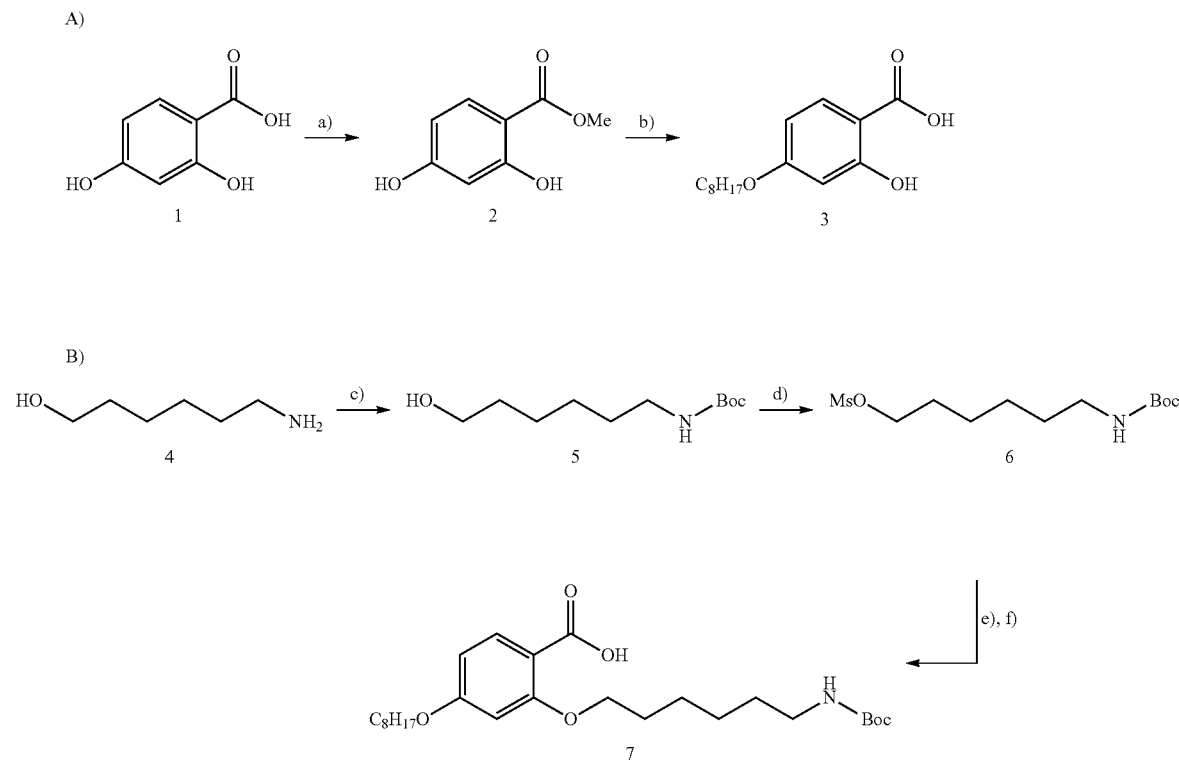

Scheme 1

C)

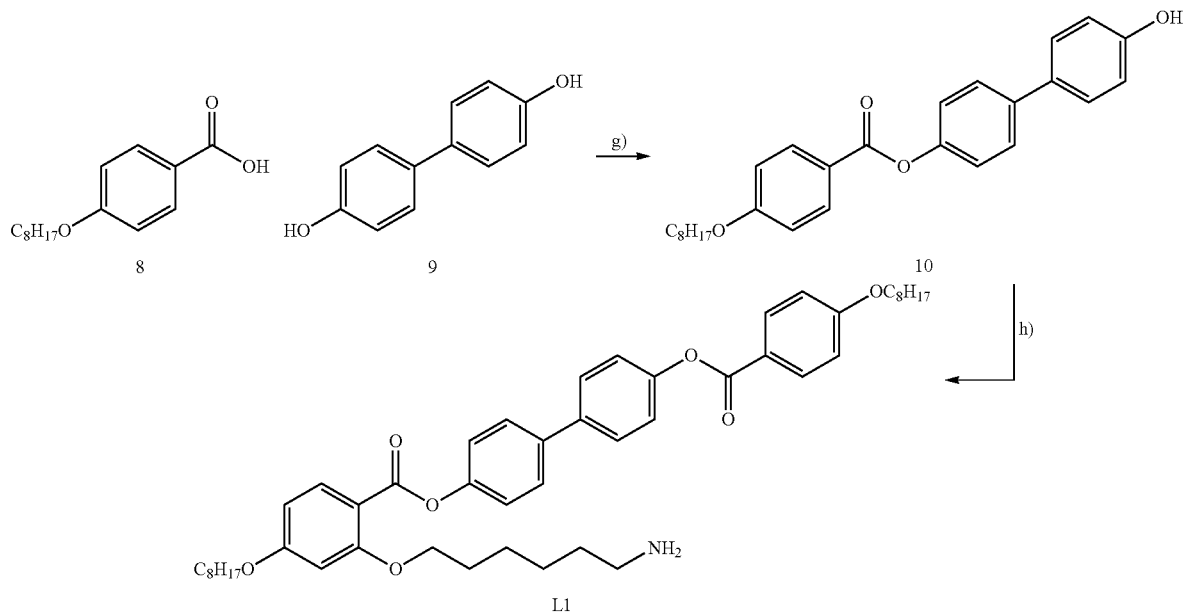

Synthesis of liquid crystal ligand L1;
a) H₂SO₄, MeOH;
b) 1-bromooctane, K₂CO₃, 2-butanone;
c) (BOC)₂O, DCM;
d) MsCl, TEA, DCM;
e) 3, KOtBu, KI, 2-butanone;
f) NaOH, MeOH;
g) DMAP, EDCl, TEA, THF;
h) 7, SOCl₂, Toluene The mesogenic ligands were synthesized according to Scheme 1 by preparation of a para-alkyated phenol 3 via esterification followed by Williamson etherification selectively at the 4-position. The ortho-functionality was then added via coupling with N-Boc mesylate 6, which was synthesized by N-protection followed by O-mesylation. The LC-ligand core was obtained by esterification with acid 8 and bis-phenol 9 to give alcohol 10, which was finally coupled to acid 7 via in situ acid chloride generation. This final coupling both activated the carboxylic acid group and removed the N-Boc protection to yield the final ligand 11.

Synthesis of 2-(3-((tert butoxycarbonyl)amino)propoxy)-4-(octyloxy)benzoic acid (12)

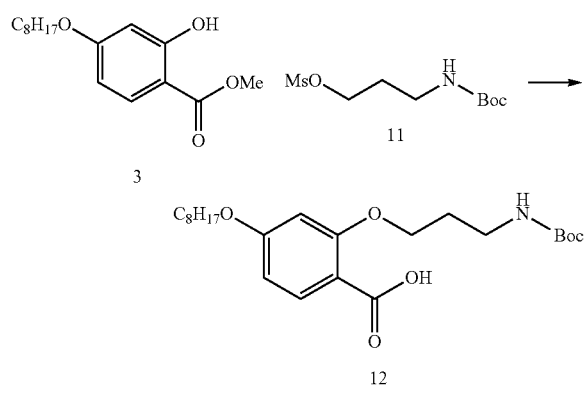

Methyl 2-hydroxy-4-(octyloxy)benzoate (3) (2 g, 7.13 mmol) was dissolved in methy-ethylketone (144 ml). This solution was added to a flask 3-((tert-butoxycarbonyl)amino)propyl methanesulfonate (11) (2.168 g, 8.56 mmol). The reaction mixture was treated with KI (1.776 g, 10.70 mmol), and KOtBu (0.961 g, 8.56 mmol) and then heated to reflux. Sample was left to heat for 16 hrs then cooled and solvent was removed under vacuum. The residue was extracted with DCM (2×50 mL) and then the combined organic fractions were dried with Na₂SO₄ and concentrated on the rotovap. The crude yellow oil was then purified by column chromatography (95:5 Hexane:EtOAc) to obtain methyl 2-(3-((tert-butoxycarbonyl)amino)propoxy)-4-(octyloxy)benzoate (2.1 g, 4.80 mmol) as a clear oil.

This sample was immediately subjected to saponification by treating it with 1M NaOH (16.00 ml, 48.0 mmol) in MeOH (96 mL) and heating the reaction at 55° C. overnight. Solvent was removed by rotovap and the residue was extracted with DCM (3×25 mL) and then the combined organic fractions were dried with Na₂SO₄ and concentrated. Crude product was recrystallized from hexanes to give 2-(3-((tert-butoxycarbonyl)amino)propoxy)-4-(octyloxy)benzoic acid (12) as a white solid (2.68 g, 6.13 mmol, 86%).

$^1$H NMR (400 MHz, Chloroform-d) δ 8.07 (d, J=8.7 Hz, 1H), 6.60 (dd, J=8.9, 2.2 Hz, 1H), 6.50 (d, J=2.4 Hz, 1H), 4.99 (d, J=7.2 Hz, 1H), 4.24 (t, J=6.2 Hz, 2H), 4.00 (t, J=6.5 Hz, 2H), 3.35 (q, J=6.3 Hz, 2H), 2.14-2.05 (m, 2H), 1.84-1.75 (m, 2H), 1.43 (s, 11H), 1.38-1.25 (m, 8H), 0.89 (t, J=6.6 Hz, 3H).

$^{13}$C NMR (101 MHz, Chloroform-d) δ 164.6, 159.1, 135.4, 110.4, 106.9, 99.7, 68.5, 31.8, 29.5, 29.3, 29.2, 29.0, 28.3, 25.9, 22.6, 14.1.

Synthesis of 4'-((4-(octyloxy)benzoyl)oxy)-[1,1'-biphenyl]-4-yl 2-(3-aminopropoxy)-4-(octyloxy)benzoate (L2)

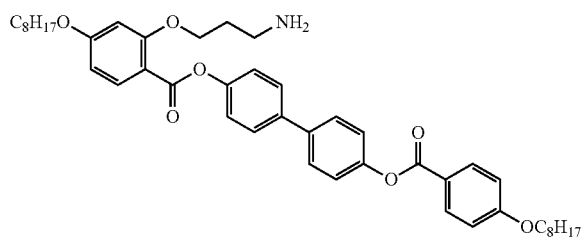

L2

Compound L2 was synthesized according to the same general procedure as used for compound L1, but substituting benzoic acid 12 in place of compound 7.

$^1$H NMR (400 MHz, Chloroform-d) δ 8.47 (s, 1H), 8.27-8.07 (m, 1H), 7.60 (ddd, J=8.7, 4.5, 1.8 Hz, 1H), 7.35-7.12 (m, 2H), 7.09-6.88 (m, 1H), 6.57 (dd, J=9.0, 2.4 Hz, 0H), 6.37 (d, J=2.4 Hz, 0H), 4.02 (dt, J=22.9, 6.8 Hz, 2H), 3.16 (d, J=8.5 Hz, 1H), 2.32-2.00 (m, 1H), 1.95-1.66 (m, 2H), 1.62-1.10 (m, 8H), 0.90 (dt, J=6.8, 3.9 Hz, 3H).

$^{13}$C NMR (101 MHz, Chloroform-d) δ=164.3, 164.2, 163.6, 163.3, 161.7, 150.9, 50.6, 137.6, 137.1, 132.1, 127.8, 122.3, 122.0, 121.9, 114.0, 111.4, 67.8, 31.9, 31.8, 31.8, 29.5, 29.4, 29.3, 29.3, 29.2, 29.1, 26.0, 25.9, 22.7, 22.6, 22.6, 13.9, 13.9, 13.8.

Synthesis of 4'-hydroxy-[1,1'-biphenyl]-4-yl 4-azido-2,3,5,6-tetrafluorobenzoate (14)

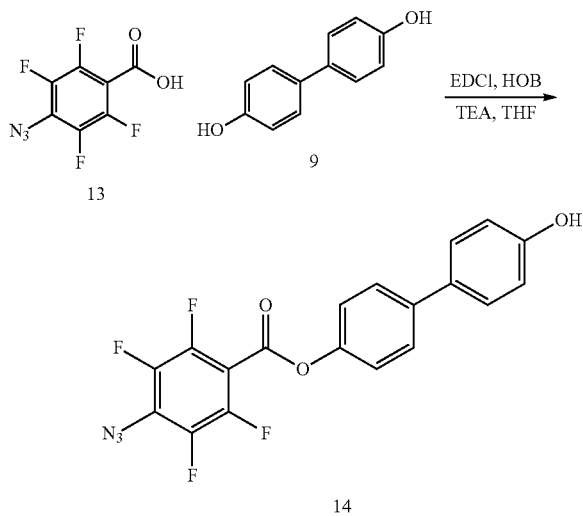

4-azido-2,3,5,6-tetrafluorobenzoic acid 13 (3.00 g, 12.76 mmol), [1,1'-biphenyl]-4,4'-diol 9 (2.17 g, 11.64 mmol), and hydroxybenzotriazole (1.90 g, 14.04 mmol) were dissolved in DCM (70 mL). The reaction was cooled to 0° C. using an ice bath and then N-methylmorpholine (4.21 mL, 38.3 mmol). Finally, 1-ethyl-3-(3-dimethylaminopropyl)carbodiimide-HCl (2.69 g, 14.04 mmol) was added and the reaction was allowed to warm to room temperature overnight, giving a milky solution. The reaction mixture was filtered and solids were washed with DCM. The filtrate was cooled to 0° C. and then quenched with saturated NH$_4$Cl. The mixture was stirred for 15 min and allowed to warm to room temperature over 15 min. The mixture was extracted with DCM (3×40 mL) and the combined organic layer was washed with 1M HCl, dried with Na$_2$SO$_4$, filtered and evaporated to dryness under vacuum. The residue was treated with MeOH (150 mL), heated to reflux, and filtered while hot. The clear filtrate was cooled to room temp to allow crystal to form, which was then isolated by filtration to yield 4'-hydroxy-[1,1'-biphenyl]-4-yl 4-azido-2,3,5,6-tetrafluorobenzoate 14 (2.32 g, 5.74 mmol 45% yield).

$^1$H NMR (400 MHz, Acetone-d6) δ 8.51 (s, 1H), 7.65 (dd, J=8.7, 1.5 Hz, 2H), 7.50 (dd, J=8.6, 1.5 Hz, 2H), 7.30 (dd, J=8.6, 1.5 Hz, 2H), 6.91 (dd, J=8.6, 1.5 Hz, 2H).

$^{13}$C NMR (101 MHz, acetone) δ 157.3, 149.0, 139.4, 131.1, 127.9, 127.3, 121.6, 115.7.

Synthesis of 4'-((2-((6-aminohexyl)oxy)-4-(octyloxy)benzoyl)oxy)-[1,1'-biphenyl]-4-yl 4-azido-2,3,5,6-tetrafluorobenzoate (L3)

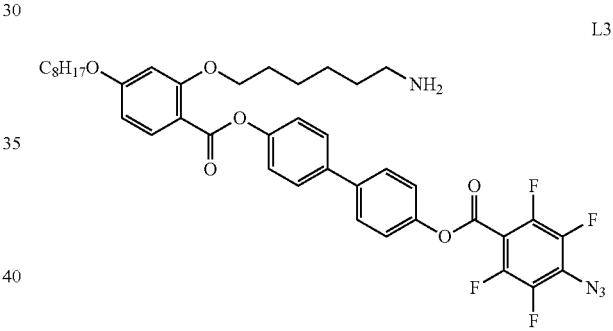

L3

2-((6-((tert-butoxycarbonyl)amino)hexyl)oxy)-4-(octyloxy)benzoic acid 7 (0.99 g, 2.335 mmol) was dissolved in toluene (13.00 mL). Thionyl chloride (0.511 mL, 7.01 mmol) was added dropwise and the reaction was stirred at room temperature for 24 hours. Conversion to the acid chloride was monitored by HPLC. Finally, 4'-hydroxy-[1,1'-biphenyl]-4-yl 4-azido-2,3,5,6-tetrafluorobenzoate 12 (0.99 g, 2.452 mmol) was added and the reaction mixture was heated to 60° C. for 24 hrs. Solvent was removed under vacuum. The residue was dissolved in iPrOH, sonicated and then removed under vacuum. This process was repeated three times, and finally suspended in iPrOH a final time. The crude solids were isolated by centrifugation and the supernatant was separated and disposed. The solids were then recrystallized from EtOH, giving 4'-((2-((6-aminohexyl)oxy)-4-(octyloxy)benzoyl)oxy)-[1,1'-biphenyl]-4-yl 4-azido-2,3,5,6-tetrafluorobenzoate L3 (0.70 g, 0.932 mmol, 39% yield) as a white powder.

$^1$H NMR (400 MHz, Chloroform-d) δ 8.15 (s, 3H), 8.02 (dd, J=8.9, 1.5 Hz, 1H), 7.60 (td, J=8.7, 4.2 Hz, 4H), 7.30-7.16 (m, 5H), 6.50 (dd, J=8.9, 2.2 Hz, 1H), 6.45 (d, J=2.4 Hz, 1H), 3.98 (dt, J=11.0, 6.2 Hz, 4H), 2.87 (d, J=9.1 Hz, 2H), 1.95 (s, 2H), 1.88-1.57 (m, 6H), 1.61-1.10 (m, 15H), 0.99-0.82 (m, 3H).

$^{13}$NMR (101 MHz, Chloroform-d) δ 168.6, 165.9, 165.1, 164.4, 163.6, 161.2, 157.6, 150.2, 149.8, 147.8, 144.3, 141.8, 139.1, 138.6, 137.9, 137.2, 134.5, 131.6, 128.1, 127.9, 127.9, 122.3, 122.1, 121.5, 109.16, 108.35, 106.8, 106.1, 104.3, 101.2, 99.4, 68.5, 68.4, 68.1, 39.1, 31.7, 31.7, 29.2, 29.1, 29.0, 28.9, 25.9, 25.8, 22.5, 13.9.

Synthesis of 4'-((2-(3-aminopropoxy)-4-(octyloxy)benzoyl)oxy)-[1,1'-biphenyl]-4-yl 4-azido-2,3,5,6-tetrafluorobenzoate (L4)

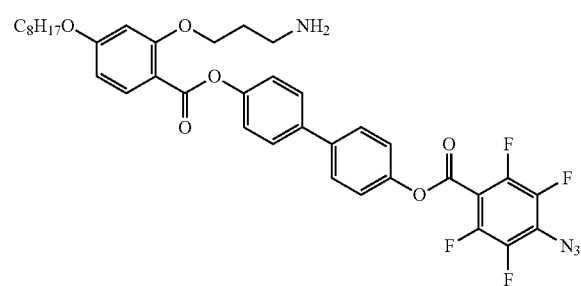

Compound L4 was synthesized according to the general protocol used for compound L3, with the substitution of the benzoic acid 12 in place of compound 7.

$^{1}$H NMR (400 MHz, Chloroform-d) δ 8.02 (d, J=8.7 Hz, 1H), 7.70-7.43 (m, 4H), 7.33-7.10 (m, 4H), 6.57-6.39 (m, 1H), 6.38-6.27 (m, 1H), 3.94 (p, J=8.5, 7.6 Hz, 4H), 3.14 (s, 2H), 2.13 (s, 2H), 1.84-1.61 (m, 2H), 1.50-1.11 (m, 12H), 0.92-0.77 (m, 3H).

$^{13}$C NMR (101 MHz, Chloroform-d) δ 168.6, 165.9, 165.1, 164.4, 163.6, 161.2, 157.6, 150.2, 149.8, 147.8, 144.3, 141.8, 139.1, 138.6, 137.9, 137.2, 134.5, 131.6, 128.1, 127.96, 127.95, 122.3, 122.1, 121.5, 109.1, 108.3, 106.8, 106.1, 104.3, 101.2, 99.4, 68.5, 68.4, 68.1, 39.1, 31.7, 31.7, 29.2, 29.2, 29.1, 29.1, 29.1, 29.0, 28.9, 28.9, 25.9, 25.8, 22.5, 13.9.

Ligand Phase Characterization

Each of the ligands synthesized were characterized initially by polarized optical microscopy and Differential Scanning calorimetry (DSC). Microscopy confirmed that both materials exhibited a smectic and nematic phase. These studies also showed that the materials could not be heated to the isotropic phase reversibly since that phase transition occurs at approx. ~180° C. and the materials were not stable at such high temperatures. This was also true in the case of the cross-linkable ligands. The materials however could be heated to more modest temperatures of ~125° C. reversibly where they remained in the smectic phase and the crystal to smectic transition was observed. Compound L2 appeared to exhibit two distinct smectic phases.

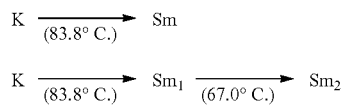

Ligand Exchange

Total particle ligand density was approximated using thermal gravimetric analysis (TGA). A sample of ODA-QD particles was dried into a TGA sample cup and exposed to a heating program of 5° C. per minute from 25° C.-1000° C. under a constant stream of compressed air. The percent reduction in mass was used to approximate the total mass of organic ligand (ODA) in the sample. Separately, the concentration of CdSe quantum dot (QD) particles was measured spectrometrically. These two values were used to approximate the total ligand coverage and number of ligand exchangeable sites for each particle.

The quantum dots (also referred to as "nanoparticles" herein) were washed using a precipitation-redispersion scheme. In the process, 1 mL of quantum dot solution was precipitated with 1 mL of methanol. The mixture was centrifuged for 10 min and the supernatant was discarded. The precipitate was then redissolved in 1 mL of toluene and washed two more times. Afterwards the precipitate was dissolved in 1 mL of chloroform. A solution of compound L1 dissolved in toluene (40 mmol) was added to the quantum dot solution, heated to 40° C., and stirred for 3 hours. The mixture was then taken off heat and left to cool back to room temperature. 2 mL ethyl acetate was then added to the ligand exchanged quantum dot solution and centrifuged. The precipitate was washed two more times using a 1:1:2 solution of toluene, chloroform, and ethyl acetate. The precipitate was finally resuspended in 1 mL toluene. Before and after the ligand exchange the particles were characterized by UV-Vis spectrometry and TGA. The QD absorption spectrum was used to produce a concentration calibration curve from 10 dilutions of the QDs before and after exchange to determine a QD yield of 87.9%. Based on mass difference before and after the exchange and assuming an upper limit of 1 to 1 ligand exchange ratio the percentage of LC ligands from total ligands was 81-70%.

Figure 6:
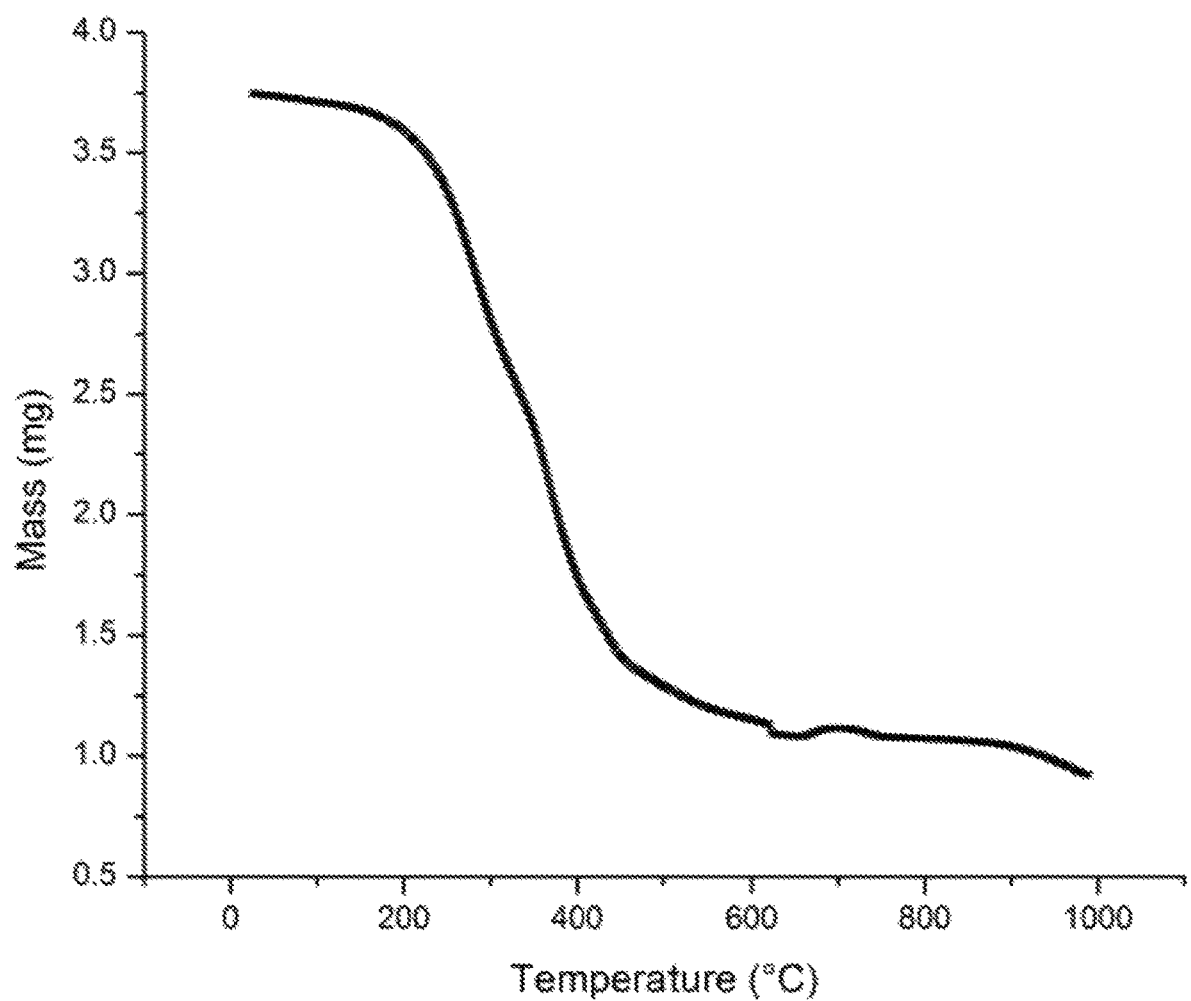
FIG. 6 shows a graph of thermal gravimetric analysis (TGA) data for the organic ligand-quantum dot (ODA-QD) particles used before ligand exchange, according to embodiments of the present disclosure. The percent reduction in mass was used to approximate the total mass of organic ligand, octadecylamine (ODA), in the sample.

FIG. 6 shows a graph of thermal gravimetric analysis (TGA) data for the organic ligand-quantum dot (ODA-QD) particles used before ligand exchange. The percent reduction in mass was used to approximate the total mass of organic ligand (ODA) in the sample.

Small Angle X-ray Scattering (SAXS)

X-ray scattering experiments were carried out on beamline 4-2 at the Stanford Synchrotron radiation light source (SSRL). An 11 keV beam was used with a beam spot size of 0.3×0.1 mm at the sample. QD shells dispersed in 5CB were filled into 1 mm quartz capillaries after formation and mounted in a transmission configuration on the beamline in a custom designed sample holder allowing translation and rotation of the capillary. Samples were exposed to the x-ray beam for 1 s at three different spots and scattering data collected on a Rayonix MX225-HE CCD detector, with 3072×3072 resolution, 73.242 μm pixel size and 2×2 binning. The data was initially corrected and analyzed using custom software at the beamline to produce 1D scattering plots of intensity as a function of scattering vector, q. Further analysis was carried out using Origin, including peak fitting and further background subtraction as necessary.

Optical Microscopy

Fluorescence microscopy was used to image the spatial distribution of the LC-QDs in the host phase. In all experiments presented here CdSe/ZnS core shell QDs with an emission wavelength centered at 620 nm were used. Fluorescence imaging was carried out on an upright Leica DM2500P microscope in reflection mode using a 20× or 40× objective. For fluorescence imaging of QDs with a peak emission at 620 nm, a 515-560 nm band-pass filter with white-light mercury lamp illumination was used. Emission was detected using a 580 nm dichroic mirror and a 590 nm Long pass filter. The microscope was also used in transition mode with a white light source with crossed polarizers to image sample birefringence. Samples were mounted on standard glass slides under a cover slip, planar liquid crystal alignment was achieved using a rubbed PVA surface coating. Transmission Electron Microscopy (TEM)

QD shells suspended in 5CB liquid crystal were drop cast onto holey carbon 200 mesh copper grids and imaged without further treatment. The samples were observed using a Jeol 2100 Cryo TEM instrument in the Materials Research Laboratory facility at the University of Illinois, Urbana-Champaign. The instrument had a 0.27 nm point to point resolution and allowed for BF/DF imaging, diffraction and high sample tilt. Real time transmission imaging of the sample was captured with a low close mode using a Gatan UltraScan 2k×2k CCD camera.

Example 3

Additional mesogenic ligands (ligands L5 to L16) were synthesized according to the procedures described above. The structures of ligands L5 to L16, including HPLC and MS characterization data, are shown in Table 1 below.

The mesogenic ligands L5 to L16 were each exchanged onto the surface of QD nanoparticles for producing three-dimensional shell structures according to the procedures described above.

Three-dimensional structures (e.g., shell structures as described herein) using QD nanoparticles exchanged with ligands L10, L12, L13 and L16, respectively, were prepared according to the procedures described above.

TABLE 1

Mesogenic Ligands

| Compound | Characterization Data |
|---|---|
| 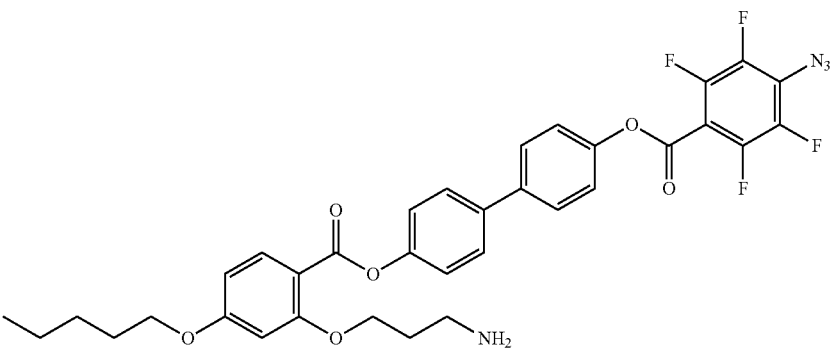 [SMILES: CCCCCOc1ccc(C(=O)Oc2ccc(-c3ccc(OC(=O)c4c(F)c(F)c(N=[N+]=[N-])c(F)c4F)cc3)cc2)c(OCCCN)c1]  4'-(2-(3-aminopropoxy)-4-(pentyloxy)benzoyloxy)biphenyl-4-yl 4-azido-2,3,5,6-tetrafluorobenzoate | L5  UV time: 2.446 min<br>Mass time: 2.502 min<br>Mass: 667.3 (666.21 + 1H) |
| 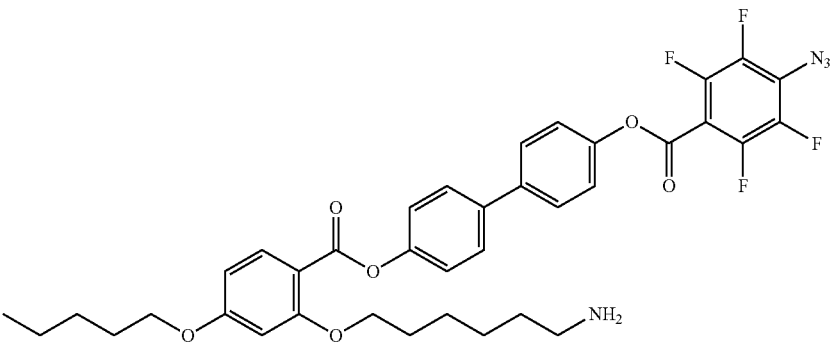 [SMILES: CCCCCOc1ccc(C(=O)Oc2ccc(-c3ccc(OC(=O)c4c(F)c(F)c(N=[N+]=[N-])c(F)c4F)cc3)cc2)c(OCCCCCCN)c1]  4'-(2-(6-aminohexyloxy)-4-(pentyloxy)benzoyloxy)biphenyl-4-yl 4-azido-2,3,5,6-tetrafluorobenzoate | L6  UV time: 2.514 min<br>Mass time: 2.575 min<br>Mass: 709.3 (708.26 + 1H) |

TABLE 1-continued

Mesogenic Ligands

| Compound | Characterization Data |
|---|---|
| 4'-(4-methoxybenzoyloxy)biphenyl-4-yl 2-(3-aminopropoxy)-4-(pentyloxy)benzoate | L7  UV time: 5.600 min<br>Mass time: 5.678 min<br>Mass: 584.3 (584.26 + 1H) |
| 4'-(4-methoxybenzoyloxy)biphenyl-4-yl 2-(6-aminohexyloxy)-4-(pentyloxy)benzoate | L8  UV time: 2.480 min<br>Mass time: 2.535 min<br>Mass: 626.3 (625.3 + 1H) |
| 4'-(4-methoxybenzoyloxy)biphenyl-4-yl 2-(3-aminopropoxy)-4-(octyloxy)benzoate | L9  UV time: 2.567 min<br>Mass time: 2.625 min<br>Mass: 626.3 (625.3 + 1H) |
| 4'-(4-methoxybenzoyloxy)biphenyl-4-yl 2-(6-aminohexyloxy)-4-(octyloxy)benzoate | L10 UV time: 6.447 min<br>Mass time: 6.528 min<br>Mass: 667.35 (668.4 + 1H) |

TABLE 1-continued

Mesogenic Ligands

| Compound | Characterization Data |
|---|---|
| 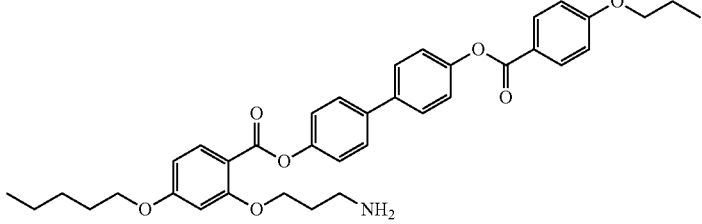<br>4'-(4-propoxybenzoyloxy)biphenyl-4-yl 2-(3-aminopropoxy)-4-(pentyloxy)benzoate | L11 UV time: 6.072 min<br>Mass time: 6.150 min<br>Mass: 612.4 (611.29 + 1H) |
| 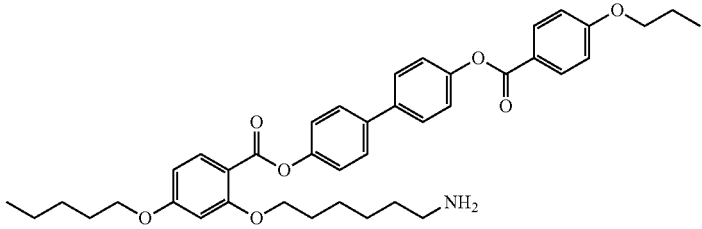<br>4'-(4-propoxybenzoyloxy)biphenyl-4-yl 2-(6-aminohexyloxy)-4-(pentyloxy)benzoate | L12 UV time: 2.677 min<br>Mass time: 2.729 min<br>Mass: 654.4 (653.34 + 1H) |
| 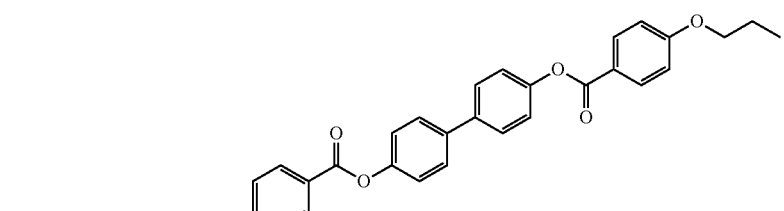<br>4'-(4-propoxybenzoyloxy)biphenyl-4-yl 2-(3-aminopropoxy)-4-(octyloxy)benzoate | L13 UV time: 6.629 min<br>Mass time: 6.713 min<br>Mass: 654.4 (653.34 + 1H) |
| 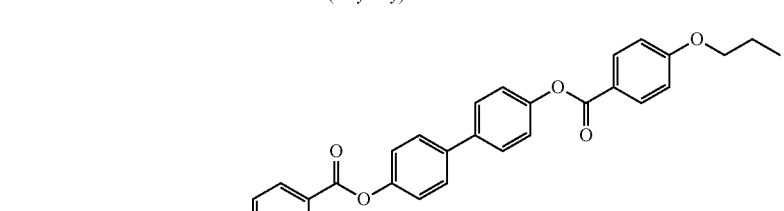<br>4'-(4-propoxybenzoyloxy)biphenyl-4-yl 2-(6-aminohexyloxy)-4-(octyloxy)benzoate | L14 UV time: 6.848 min<br>Mass time: 6.929 min<br>Mass: 696.5 (695.38 + 1H) |
| 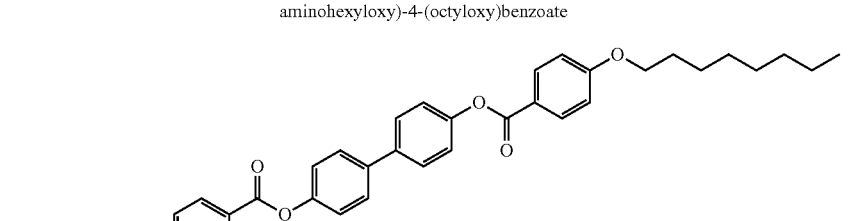<br>4'-(4-(octyloxy)benzoyloxy)biphenyl-4-yl 2-(3-aminopropoxy)-4-(pentyloxy)benzoate | L15 UV time: 6.965 min<br>Mass time: 7.050 min<br>Mass: 682.4 (681.37 + 1H) |

TABLE 1-continued

Mesogenic Ligands

| Compound | Characterization Data |
|---|---|
| 4'-(4-(octyloxy)benzoyloxy)biphenyl-4-yl 2-(6-aminohexyloxy)-4-(pentyloxy)benzoate | L16 UV Time: 7.361 min<br>Mass Time: 7.451 min<br>Mass: 724.4 (723.41 + 1H) |

Example 4

Mesogenic ligands L5, L6, L7, L8, L9, L11, L14 and L15 were each exchanged onto the surface of QD nanoparticles for producing three-dimensional shell structures according to the procedures described above.

Three-dimensional structures (e.g., shell structures as described herein) using QD nanoparticles exchanged with ligands L5, L6, L7, L8, L9, L11, L14 and L15, respectively, are prepared according to the procedures described above.

Although the foregoing embodiments have been described in some detail by way of illustration and example for purposes of clarity of understanding, it is readily apparent to those of ordinary skill in the art in light of the teachings of the present disclosure that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A three-dimensional shell structure, comprising a plurality of stably associated mesogenic ligand-functionalized nanoparticles, wherein the shell structure has a surface that at least partially encloses a space or a material.

2. The structure of claim 1, wherein the surface that at least partially encloses the space or the material is a spherical surface.

3. The structure of claim 1, wherein the structure has at least one dimension of 0.01 μm to 10 μm.

4. The structure of claim 2, wherein the spherical surface has an average diameter of 0.01 μm to 10 μm.

5. The structure of claim 1, wherein the nanoparticles have an average diameter of 1 nm to 100 nm.

6. The structure of claim 1, wherein the nanoparticles are composed of one or more material selected from the group consisting of a semiconductor material, a metal, a metal oxide, a metalloid, an oxide, a magnetic material, and a polymer.

7. The structure of claim 1, wherein the structure is composed of nanoparticles having substantially the same physical and chemical characteristics.

8. The structure of claim 1, wherein the structure is composed of nanoparticles having different physical and/or chemical characteristics.

9. The structure of claim 1, wherein the mesogenic ligand-functionalized nanoparticles comprise a mesogenic ligand attached to a surface of the nanoparticles.

10. The structure of claim 9, wherein the mesogenic ligand comprises a cross-linkable functional group.

11. The structure of claim 10, wherein the cross-linkable functional group is a light activated cross-linkable functional group.

12. A three-dimensional shell structure, comprising a plurality of stably associated mesogenic ligand-functionalized nanoparticles, wherein the mesogenic ligand-functionalized nanoparticles comprise a mesogenic ligand attached to a surface of the nanoparticles, and the mesogenic ligand has a structure of formula (I):

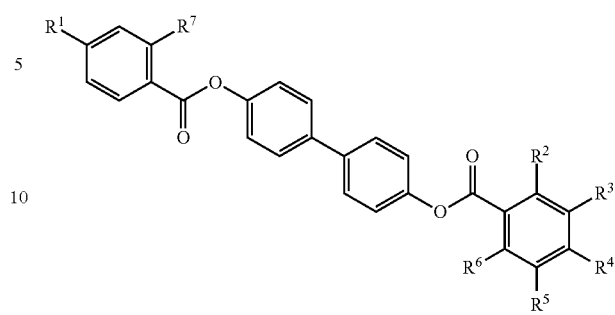

(I)

wherein
$R^1$ to $R^7$ are each independently selected from H, halo, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, and substituted heteroaryl, and wherein the shell structure has a surface that at least partially encloses a space or a material.

13. A three-dimensional shell structure, comprising a plurality of stably associated mesogenic ligand-functionalized nanoparticles, wherein the mesogenic ligand-functionalized nanoparticles comprise a mesogenic ligand attached to a surface of the nanoparticles, and the mesogenic ligand is selected from the group consisting of:

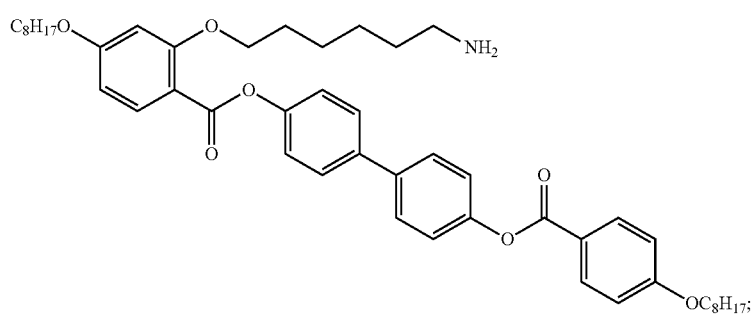

(L1)

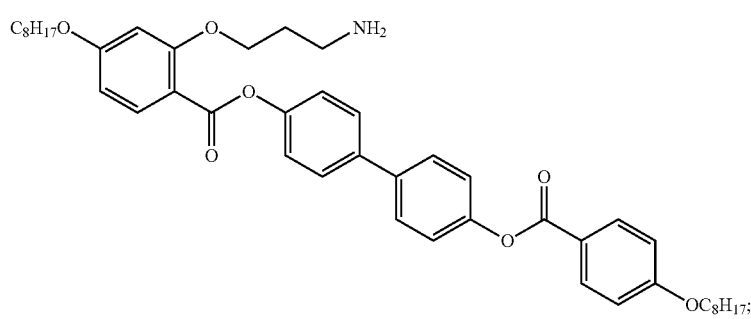

(L2)

-continued
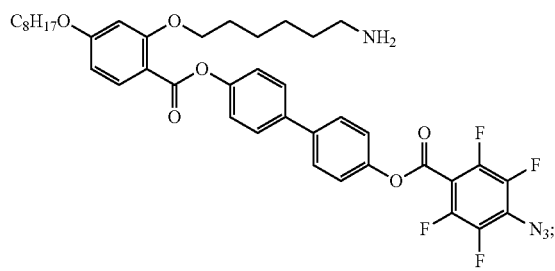 (L3)
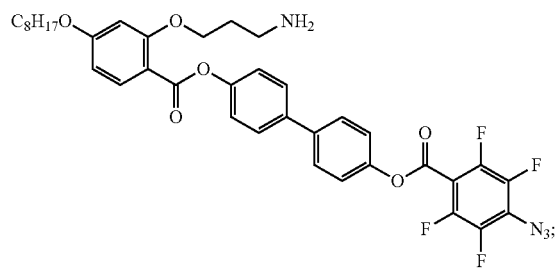 (L4)
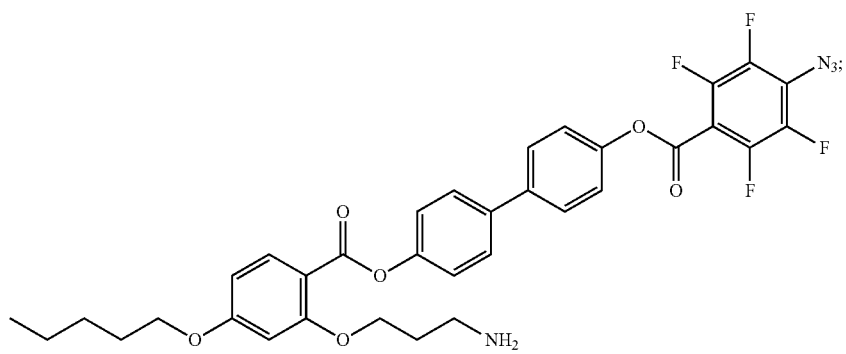 (L5)
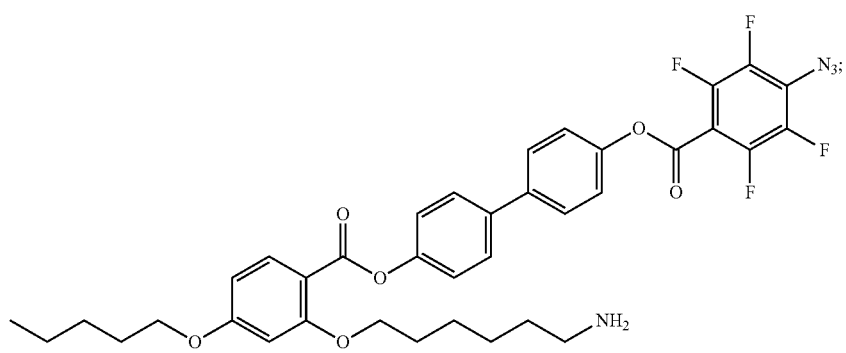 (L6)
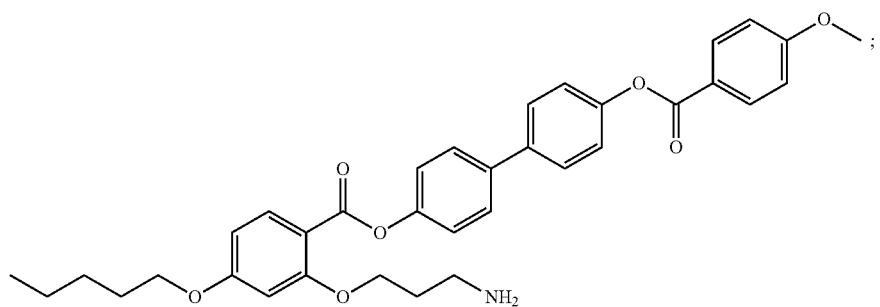 (L7)
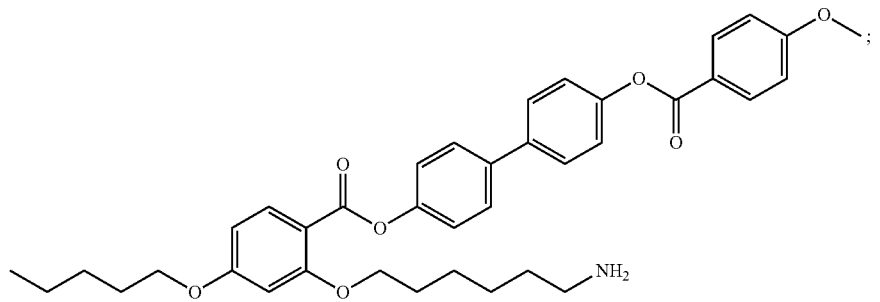 (L8)

-continued
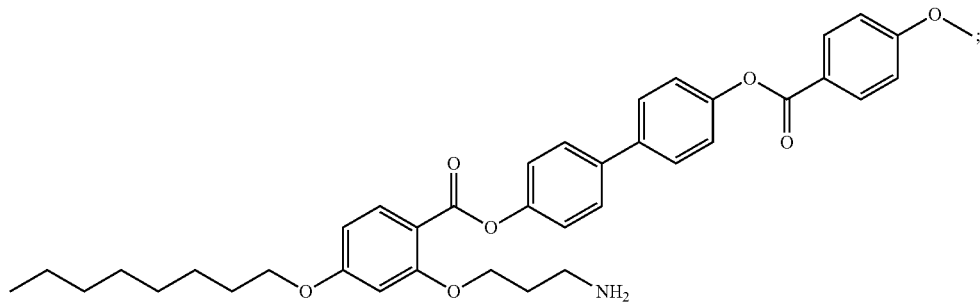
(L9)
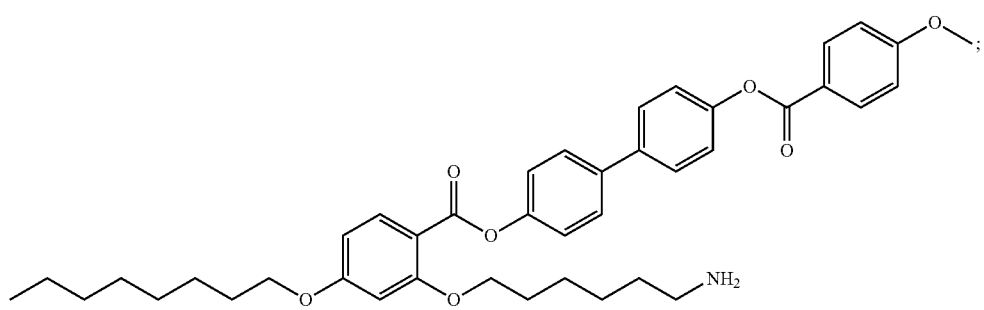 [SMILES: CCCCCCCCOc1ccc(C(=O)Oc2ccc(-c3ccc(OC(=O)c4ccc(OC)cc4)cc3)cc2)c(OCCCCCCN)c1]
(L10)
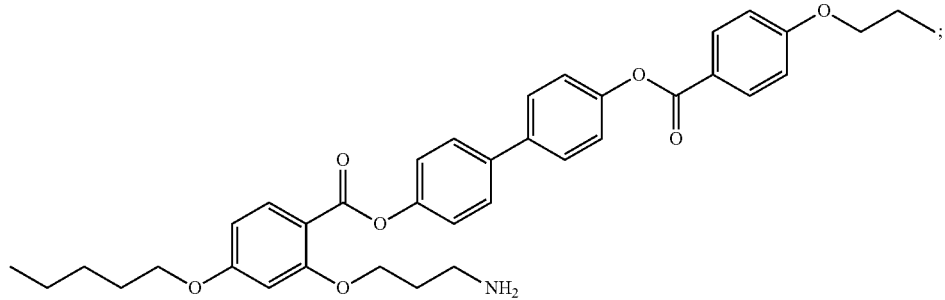
(L11)
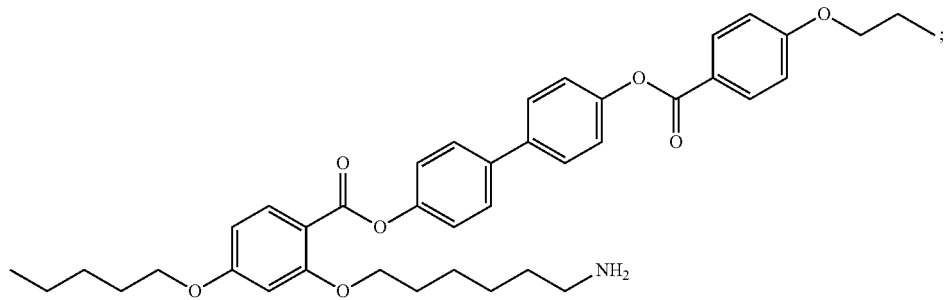
(L12)
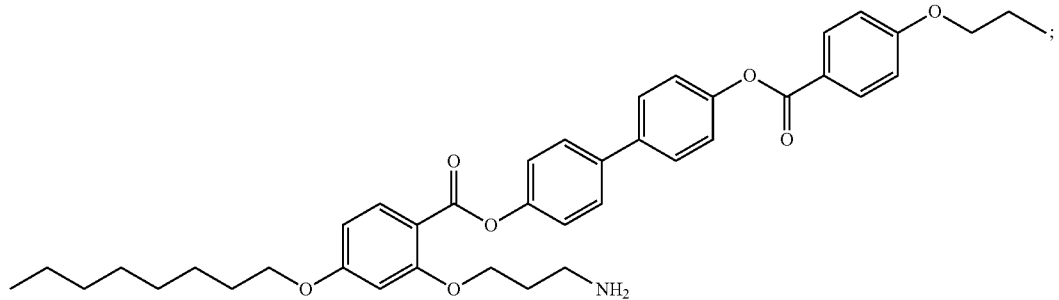
(L13)

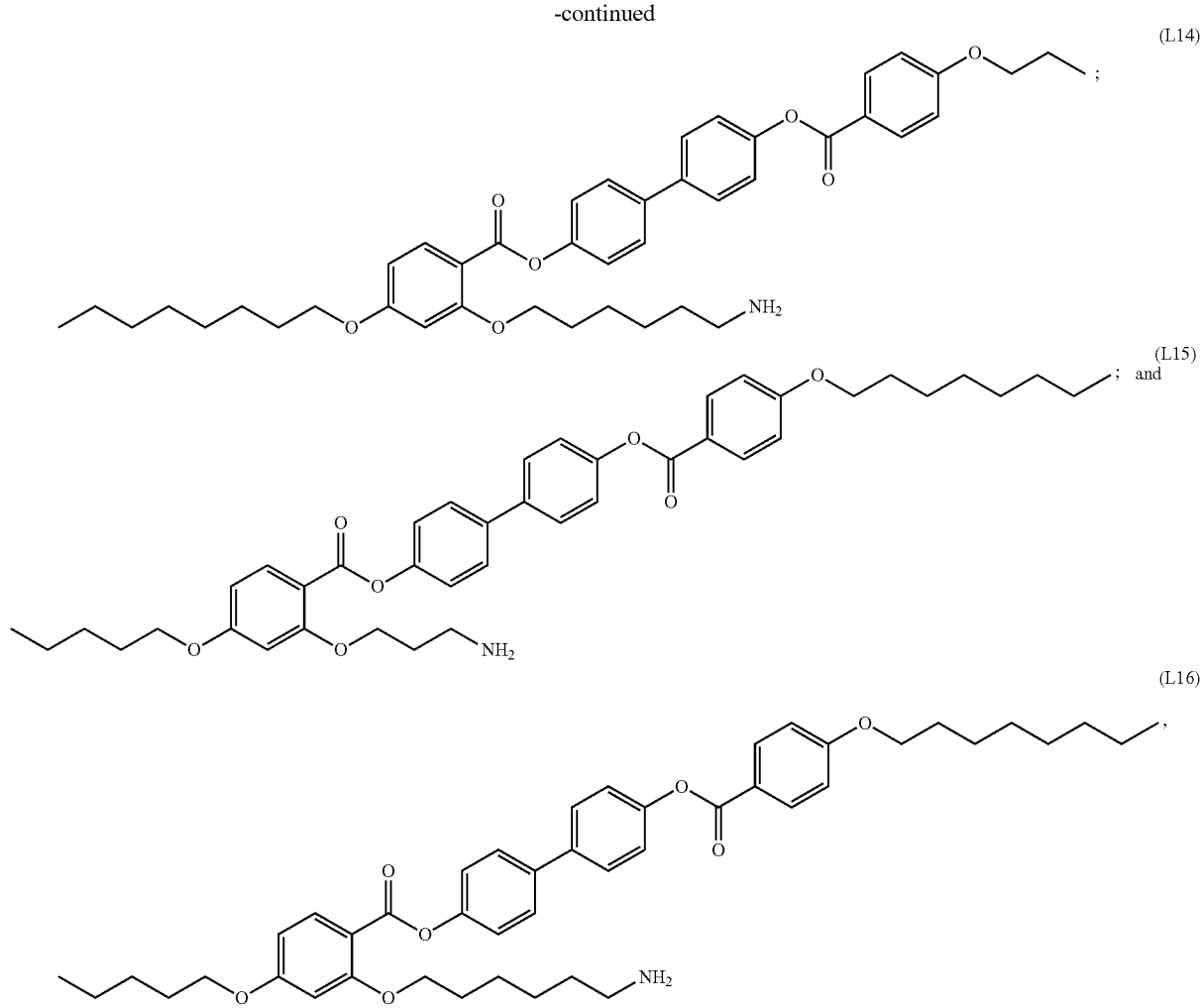

and
wherein the shell structure has a surface that at least partially encloses a space or a material.

14. The structure of claim 1, further comprising an active agent encapsulated inside the structure.

15. The structure of claim 1, further comprising an ink encapsulated inside the structure.

16. A composition comprising:
a liquid; and
a structure of claim 1 in the liquid.

17. The composition of claim 16, wherein the liquid is an organic solvent.

18. A composition for producing a three-dimensional shell structure of stably associated mesogenic ligand-functionalized nanoparticles, the composition comprising:
mesogenic ligand-functionalized nanoparticles; and
a liquid crystalline liquid,
wherein the composition is sufficient for producing a three-dimensional shell structure comprising a plurality of stably associated mesogenic ligand-functionalized nanoparticles, wherein the shell structure has a surface that at least partially encloses a space or a material.

19. The composition of claim 18, wherein a mesogenic ligand of the mesogenic ligand-functionalized nanoparticles has a phase transition temperature greater than the phase transition temperature of the liquid crystalline liquid.

20. A method of producing a three-dimensional shell structure of stably associated mesogenic ligand-functionalized nanoparticles, the method comprising:
dispersing mesogenic ligand-functionalized nanoparticles in a liquid crystalline liquid; and
inducing a phase transition in the liquid crystalline liquid to produce a three-dimensional shell structure of stably associated mesogenic ligand-functionalized nanoparticles, wherein the shell structure has a surface that at least partially encloses a space or a material.

21. The method of claim 20, wherein the dispersing comprises applying sound energy to the mesogenic ligand-functionalized nanoparticles in the liquid crystalline liquid.

22. The method of claim 20, wherein the inducing comprises reducing the temperature of the liquid crystalline liquid.

23. The method of claim 20, wherein the phase transition in the liquid crystalline liquid is a phase transition from an isotropic phase to a nematic phase.

24. The method of claim 20, further comprising crosslinking the mesogenic ligand-functionalized nanoparticles in the three-dimensional structure.

25. The method of claim 24, wherein the mesogenic ligand-functionalized nanoparticles comprise a light activated cross-linkable functional group, and the crosslinking comprises applying light to the nanoparticles sufficient to activate the light activated cross-linkable functional group and produce one or more crosslinks between the nanoparticles.

26. A composition comprising a three-dimensional structure of stably associated mesogenic ligand-functionalized nanoparticles produced by the method of claim 20.

27. A light emitting device comprising:
a substrate; and
a structure of claim 1 on a surface of the substrate.

28. The device of claim 27, wherein the device is a component of a video display or a light.

29. The structure of claim 1, wherein the plurality of stably associated mesogenic ligand-functionalized nanoparticles completely encloses the space or the material.

30. The structure of claim 1, wherein the plurality of stably associated mesogenic ligand-functionalized nanoparticles are stably associated with each other through non-covalent interactions.

31. The structure of claim 1, wherein the plurality of stably associated mesogenic ligand-functionalized nanoparticles are stably associated with each other through covalent interactions.

32. The structure of claim 1, wherein the plurality of stably associated mesogenic ligand-functionalized nanoparticles are stably associated with each other through a combination of non-covalent and covalent interactions.

* * * * *

UNITED STATES PATENT AND TRADEMARK OFFICE
CERTIFICATE OF CORRECTION

| | | |
|---|---|---|
| PATENT NO. | : 10,774,262 B2 | Page 1 of 1 |
| APPLICATION NO. | : 15/535259 | |
| DATED | : September 15, 2020 | |
| INVENTOR(S) | : Hirst et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 38 days.

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*